US009320877B2

(12) United States Patent
Imran

(10) Patent No.: US 9,320,877 B2
(45) Date of Patent: Apr. 26, 2016

(54) SOLID DRUG DELIVERY APPARATUS AND FORMULATIONS AND METHODS OF USE

(75) Inventor: Mir Imran, Los Altos Hills, CA (US)

(73) Assignee: INCUBE LABS, LLC, San Jose, CA (US)

(*) Notice: Subject to any disclaimer, the term of this patent is extended or adjusted under 35 U.S.C. 154(b) by 327 days.

(21) Appl. No.: 13/138,764

(22) PCT Filed: Mar. 22, 2010

(86) PCT No.: PCT/US2010/000851
§ 371 (c)(1),
(2), (4) Date: Jul. 13, 2012

(87) PCT Pub. No.: WO2010/107507
PCT Pub. Date: Sep. 23, 2010

(65) Prior Publication Data
US 2012/0296259 A1    Nov. 22, 2012

Related U.S. Application Data

(60) Provisional application No. 61/210,579, filed on Mar. 20, 2009, provisional application No. 61/210,554, filed on Mar. 20, 2009.

(51) Int. Cl.
*A61M 31/00* (2006.01)
*A61M 37/00* (2006.01)
*A61M 25/00* (2006.01)

(52) U.S. Cl.
CPC ......... *A61M 31/002* (2013.01); *A61M 37/0069* (2013.01); *A61M 37/0092* (2013.01); *A61M 25/00* (2013.01)

(58) Field of Classification Search
CPC .............. A61K 9/0024; A61K 9/0009; A61M 5/14276; A61M 31/002; A61M 2205/0244; A61M 2202/0464; A61M 2205/0266; A61M 37/0069; A61M 5/1723

USPC ................... 604/890.1–892.1, 500, 503, 504, 604/65–67, 20, 502
See application file for complete search history.

(56) References Cited

U.S. PATENT DOCUMENTS 5,542,935 A    8/1996  Unger et al.
5,925,012 A    7/1999  Murphy-Chutorian et al.
(Continued)

FOREIGN PATENT DOCUMENTS

EP      1070519 A1      1/2001
WO      WO 2005/113067 A2    12/2005
WO      WO 2005/113067 A3    9/2006

OTHER PUBLICATIONS

European search report and opinion dated Jul. 20, 2012 for EP Application No. 10753826.6.
(Continued)

*Primary Examiner* — Phillip Gray
(74) *Attorney, Agent, or Firm* — Wilson Sonsini Goodrich & Rosati

(57) ABSTRACT

Embodiments provide apparatus and methods for delivering solid form medications such as pellets to various locations in the body. One embodiment provides an apparatus for in vivo delivery of medication pellets comprising a first chamber including an opening; a second chamber substantially surrounding the first chamber, a carriage disposed in the first chamber, a mechanism for transferring the medication pellets from the first chamber to the second chamber and a pusher plate. The carriage can hold and dispense a plurality of medication pellets. Each pellet contains a selected dose of drug to treat a medical condition. A catheter is positioned in the second chamber. The catheter has a lumen sized for the pellet, a proximal end inside the chamber and a distal end extending through chamber opening to deliver the pellet to a delivery site. The pusher plate engages and advances the pellet though the catheter to the delivery site.

45 Claims, 22 Drawing Sheets

(56) References Cited

U.S. PATENT DOCUMENTS

| | | | |
|---|---|---|---|
| 6,142,972 | A | 11/2000 | Cheikh |
| 6,468,263 | B1 | 10/2002 | Fischell et al. |
| 6,497,699 | B1* | 12/2002 | Ludvig ............ A61M 5/14276 604/67 |
| 2002/0026108 | A1 | 2/2002 | Colvin |
| 2002/0068084 | A1 | 6/2002 | Staniforth |
| 2003/0049865 | A1* | 3/2003 | Santini, Jr. ............ A61B 5/00 436/518 |
| 2003/0064097 | A1* | 4/2003 | Patel .................... A61K 9/1617 424/465 |
| 2004/0106914 | A1* | 6/2004 | Coppeta ............... A61K 9/0004 604/892.1 |
| 2005/0107753 | A1 | 5/2005 | Rezai et al. |
| 2005/0182389 | A1 | 8/2005 | Laporte et al. |
| 2006/0035914 | A1 | 2/2006 | Hochman |
| 2006/0129050 | A1 | 6/2006 | Martinson et al. |
| 2006/0129225 | A1 | 6/2006 | Kopia et al. |
| 2006/0178655 | A1 | 8/2006 | Santini et al. |
| 2006/0233941 | A1 | 10/2006 | Olson |
| 2006/0271020 | A1 | 11/2006 | Huang et al. |
| 2007/0196361 | A1 | 8/2007 | Soon-Shiong et al. |
| 2007/0243228 | A1 | 10/2007 | McKay |
| 2007/0275035 | A1* | 11/2007 | Herman ............... A61K 9/0024 424/426 |

OTHER PUBLICATIONS

International search report and written opinion dated May 26, 2010 for PCT/US2010/000851.

* cited by examiner

Pre Energy/Force Delivery

Post Energy/Force Delivery

SOLID DRUG DELIVERY APPARATUS AND FORMULATIONS AND METHODS OF USE

RELATIONSHIP TO OTHER APPLICATIONS

This application claims the benefit of priority to U.S. Provisional Application Ser. No. 61/210,554, filed Mar. 20, 2009, entitled "Solid Drug Delivery Apparatus" which is incorporated by reference herein in its entirety for all purposes. This application also claims the benefit of priority to U.S. Provisional Application Ser. No. 61/210,579, filed Mar. 20, 2009, entitled "Methods of Solid Drug Delivery" which is fully incorporated by reference herein in its entirety for all purposes.

BACKGROUND

Field of the Invention

Embodiments of the invention relate to drug delivery devices and methods of use thereof. More specifically, embodiments of the invention relate to implantable drug delivery devices for the delivery of solid form drugs and other therapeutic agents.

The current trend in many medical treatments requires the delivery of a drug to a specific target site so as to avoid the toxicity to other tissue, as well as more precisely controlling the timing and amount of drug delivered to that site. In many cases, this can require an implantable drug pump. However, due to their size and power requirements the current available pumps do not lend themselves to all medical applications, particularly for delivery of medication to the brain and other tissues, where very precisely controlled doses of drug can be required. Also current devices can require frequent replenishment of the drug due to limited reservoir size and/or limited shelf life of the drug. Thus, there is a need for improved implantable drug delivery devices and associated methods for in vivo drug delivery.

BRIEF SUMMARY

Embodiments of the invention provide apparatus, systems, formulations and methods for delivering medications in solid form to various locations in the body. Many embodiments provide an implanted apparatus for delivering medication in solid form wherein the medication includes one or more solid form drugs for treating various medical conditions such as epilepsy and diabetes. Particular embodiments provide an enclosed implanted apparatus for delivering solid form medications such as elements (e.g., pellets) to a delivery site so as to treat a medical condition for an extended period of time. Embodiments also provide various solid form medications or formulations comprising one or more drugs to be delivered by embodiments of the apparatus or other solid drug delivery apparatus.

One embodiment provides an apparatus for in vivo delivery of solid form medications or formulations comprising a first chamber including a first opening; a second chamber substantially surrounding the first chamber, a carriage disposed in the first chamber, a mechanism for transferring the medication from the first chamber to the second chamber and a pusher plate. The medication will typically be formulated into pellets, though other solid formulations are also contemplated (e.g., powder). Each pellet contains a selected dose of a drug to treat a particular medical condition such as epilepsy. The dose can be selected based on the patient's weight and age. Also, the medication pellets are desirably formulated using one or more pharmaceutical excipients, including disintegrants so as disintegrate and dissolve the pellets in a controlled fashion to achieve and maintain a sufficient concentration of the drug (either at the tissue site, plasma or other tissue location) for treatment of the condition. The pellets are also desirably fabricated so as to have a shelf life of years or longer in vivo so the drug maintains its potency and therapeutic effectiveness. The pellets can include a plurality of drugs for treatment of conditions, for example, a cocktail of antiviral drugs for treatment of HIV AIDS.

The carriage is configured to hold and dispense a plurality of medication pellets through an opening in the carriage. The carriage can be spring loaded or use other advancement means. Desirably, the carriage contains a sufficient supply of medication pellets to provide treatment of the condition for an extended period of time, for example, two years or longer.

The mechanism is disposed in the first chamber and includes a carrying member configured to receive a medication pellet from the carriage, transfer the pellet outside the first chamber through the first opening and then return inside the first chamber. Typically, the carrying member will include a slot or other opening for holding the pellet. Also a sliding member can be positioned over the carrying member to hold the pellet in place during movement of the carrying member. The carrying member and/or the sliding member can be advanced by means of a mechanical drive source such as a spring or an electrical drive source such as linear induction motor, a solenoid or a piezoelectric transducer. In specific embodiments, the drive source can comprise a nickel titanium wire or other shape memory material that changes length in response to heating from an electrical current. Use of an expandable gas as a drive source is also contemplated whereby the gas can be expanded by heating from a resistive heating element. The gas can be used to expand a piston or like drive element which engages one or more of the carrying member or the sliding member.

An elongate member such as a catheter is positioned in the second chamber. The elongate member has a lumen sized to receive the medication pellet, a proximal end inside the chamber and a distal end or tip that extends through an opening in the chamber to deliver the pellet to a target tissue site. Desirably, the distal tip has an atraumatic configuration to allow for extended periods of implantation at the target tissue site. The pusher plate is used to disengage the pellet from the mechanism and push or advance the pellet into the elongate member lumen and out to the target tissue site. The pusher plate can be coupled to one or more drive sources described herein. Other advancement means are also contemplated including use of a liquid coupled to a pump or other pressure source where the liquid carries the pellet out of the elongate member.

In many embodiments, the apparatus is coupled to a controller for controlling one more aspects of the medication delivery process including actuation and control of the drive source to deliver a medication pellet. The controller can be programmed to include a delivery regimen wherein medication is delivered at regular intervals (e.g., once or twice a day, etc) over an extended period. It can also be configured to receive a signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of angina) or longer term changes in the patient's condition or diagnosis.

The controller can be coupled to or otherwise receive inputs from an implanted sensor, such as a glucose sensor, which senses a physiologic parameter indicative of a condition to be treated by the medication in the medication pellet, for example, diabetic hyperglycemia (treated by insulin). When the controller receives an input from the sensor indicative of the condition, it initiates the delivery of one or more medication pellets to the target tissue site so as to treat the medical condition. Both the initial and subsequent inputs from the sensor can be used to titrate the delivery of medication pellets over an extended period until the condition is dissipated or otherwise treated. The controller can also receive inputs from other sensors configured to measure the plasma or other tissue concentration of the delivered drug. These inputs can also be used to titrate the delivery of the medication to achieve a selected concentration of drug (e.g., in plasma, tissue, etc). The drug sensors can be positioned at the target tissue site as well as other sites in the body (e.g., a vein or artery) in order to develop a pharmacokinetic model of the distribution of the drug at multiple sites in the body. The apparatus can also include a sensor coupled to the controller which indicates when the medication pellets have been used up and/or exactly how many are left. The controller in turn can signal this data to an external communication device such as a cell phone, portable monitor or remote monitor (e.g., at the physician's office). In this way, the patient and/or medical care provider can take appropriate action before the apparatus runs out of medication.

The pellets or other solid form of the medication are delivered to a delivery site such as subcutaneous tissue where they are configured to be broken, disintegrate and absorbed by body tissue fluids so as to produce a desired concentration of the drug at a target tissue site. In some applications, the delivery site can be the same as the target site, for example the brain. In other applications, the target site can be different from the delivery site, for example, the delivery site can be intramuscular tissue in the chest and the target site can be the heart or the liver. The delivery site can be adjacent the target site, for example adipose to deliver to underlying muscle tissue, or it can be placed at a non-oppositional site, for example, intramuscular delivery to reach the site of the heart. In each case, the medication pellet can include a selected dose of drug and be configured to disintegrate and be dissolved by body tissue fluids so as to yield a therapeutically effective concentration of the drug at the target tissue site. In many applications, this involves the pellet being dissolved by body tissue fluids at the delivery site (e.g., interstitial fluids) where the drug then diffuses from the tissue into the blood stream where it is carried to the target tissue site. Accordingly, in these and other applications, the dose of the drug in the pellet can be titrated to achieve a selected plasma (or other tissue compartment) concentration of the drug (or concentration range) for a selected period during and after dissolution of the pellet.

In some embodiments, the pellet (including the drug dose) is configured to disintegrate and be dissolved by the tissue fluids within a body compartment such as the cerebrospinal fluid (CSF) in the brain so as to achieve a selected concentration in the tissue fluid within that compartment. In particular embodiments for treating various neural disorders such as epileptic and other seizures, the pellet is configured to rapidly disintegrate and be dissolved in the CSF so as to rapidly achieve a selected concentration of the drug throughout the CSF bathing the brain to prevent the occurrence of the seizure or lessen its duration and severity. This can be achieved through the use of one or more super disintegrants as well as disintegrating enhancing features (e.g., pores, cracks or other intrusions) in or on the pellet. It can also be achieved by treating the pellet prior or after delivery with mechanical, electromagnetic, acoustical or other energy to weaken the pellet structure, create cracks and other structural defects for the ingress of fluids or initiate the breakup of the pellet into smaller pieces. In other embodiments, a solid form medication for delivery within the body of a patient is provided, the medication comprising at least one drug for the treatment of a disease or condition, wherein the medication has a shape and material properties so as to be: (i) be stored in a container implanted within the body for an extended period without substantial degradation or deleterious effect to the medication, (ii) delivered to a delivery site, and (iii) dissolve in tissue fluids at the delivery site to produce a therapeutic effect at a target tissue site to treat the disease or condition.

In various applications, embodiments of the invention can be used to deliver solid form drugs to provide treatment for a number of medical conditions including epileptic seizures, high blood pressure, elevated cholesterol, diabetes, coronary arrhythmia's (both atrial and ventricular), coronary ischemia (e.g., from a heart attack), cerebral ischemia, stroke, anemia or other like condition. The apparatus can be implanted at or near the target tissue site (e.g., the brain) or at remote delivery site (e.g., intramuscularly in the chest or thigh). Further embodiments of the invention can be used to provide concurrent treatment for two or more of these or other conditions eliminating the need for the patient to take multiple doses of multiple drugs (e.g., orally or by parenteral means) over the course of day. This is particularly beneficial to patients who have long term chronic conditions including those who have impaired cognitive abilities.

In an exemplary embodiment of a method for using the invention, depending upon the condition to be treated, the apparatus can be implanted at a selected delivery site (e.g., the brain). Implantation can be done using an open or minimally invasive surgical procedure. Prior to implantation, the carriage can be loaded with a selected number of pellets to provide for delivery of pellets to the delivery site over an extended period of time, e.g., years. Once implanted, the pellets can be stored in the apparatus for an extended period of years (e.g., 1, 2, 5 years or longer) without degradation or deleterious effect to the pellets (e.g., loss of drug potency or therapeutic effectiveness). The apparatus can deliver solid form medication to the delivery site at regular intervals (e.g., once a day, week, month, etc.) or in response to an input from a sensor. In the latter case, the input can be indicative of a particular medical condition or event such as an epileptic seizure or pre-seizure event. A controller described herein can be used to determine when to initiate delivery based on the sensor input and/or the time intervals for delivery for embodiments employing delivery at regular intervals. In either case, the controller can send a signal to the transfer mechanism to transfer a pellet from the carriage and inner chamber to outer chamber. Once in the outer chamber, the pusher plate or other advancement means transfers the pellet from the transfer mechanism and advances it out through the catheter to target delivery site. There it disintegrates/degrades and is dissolved in local tissue fluids to treat a local target tissue site (e.g., it dissolves in the CSF to treat the brain), or it is subsequently absorbed into the blood stream where it is carried to a remote target tissue site (e.g., the liver, heart, etc) or both. Further pellets can be delivered based on input from a sensor providing physiologic data predictive of the medical condition (e.g., blood glucose) or another sensor that is configured to sense the local and/or plasma concentration of the drug. In some embodiments, pellet delivery can be controlled by sensing the state of disintegration of previously delivered pellets. For example, another pellet can be delivered when it has been determined that the previous pellet is in a particular state of disintegration (e.g., it has been completely or substantially disintegrated). This can be achieved by sending and receiving a signal from the pellet such as an optical, ultrasound or electrical signal. For example, for the use of optical signal reflectance measurements can be used to determine the state of disintegration. A particular disintegration state can be determined when the reflectance signal falls below a particular threshold. Similar approaches can be used for use of reflected ultrasound or impedance. The pellet can even include various echogenic, or optically opaque or other agents to enhance the reflected ultrasonic, optical or other signal. The pellet may also include various optical indicia having one or more of a pattern, size or shape configured to provide an indication of the state of disintegration of the pellet.

Further details of these and other embodiments and aspects of the invention are described more fully below, with reference to the attached drawing figures.

BRIEF DESCRIPTION OF THE DRAWINGS

FIG. 9a shows placement of the entire apparatus in the brain for delivery of medication to a target site in brain tissue; FIG. 9b shows placement of the apparatus on the scalp with a delivery catheter extending into the brain; FIG. 9c shows an embodiment of the apparatus having two delivery catheters positioned at two different delivery sites. FIG. 9d shows an embodiment of the apparatus having two delivery catheters with the first delivery catheter positioned near or in the knee joint and the second delivery catheter positioned at a different location.

FIG. 13a shows the pellet before force/energy delivery; and FIG. 13b show the pellet afterwards.

DETAILED DESCRIPTION OF THE INVENTION

Embodiments of the invention provide apparatus, systems, formulations and methods for delivering medications in solid form to various locations in the body. Many embodiments provide an implanted apparatus for delivering medication in solid form wherein the medication includes one or more solid form drugs or other therapeutic agent for treating various medical conditions such as epilepsy, diabetes, high blood pressure, and high cholesterol. Particular embodiments provide an enclosed implanted apparatus for delivering solid form medications to a delivery site DS and ultimately to a target tissue site TS (herein target site TS), such as the brain, to treat a medical condition for an extended period of time. Embodiments also provide various solid form medications or formulations comprising one or more drugs to be delivered by embodiments of the apparatus or other solid drug delivery apparatus.

Figure 1:
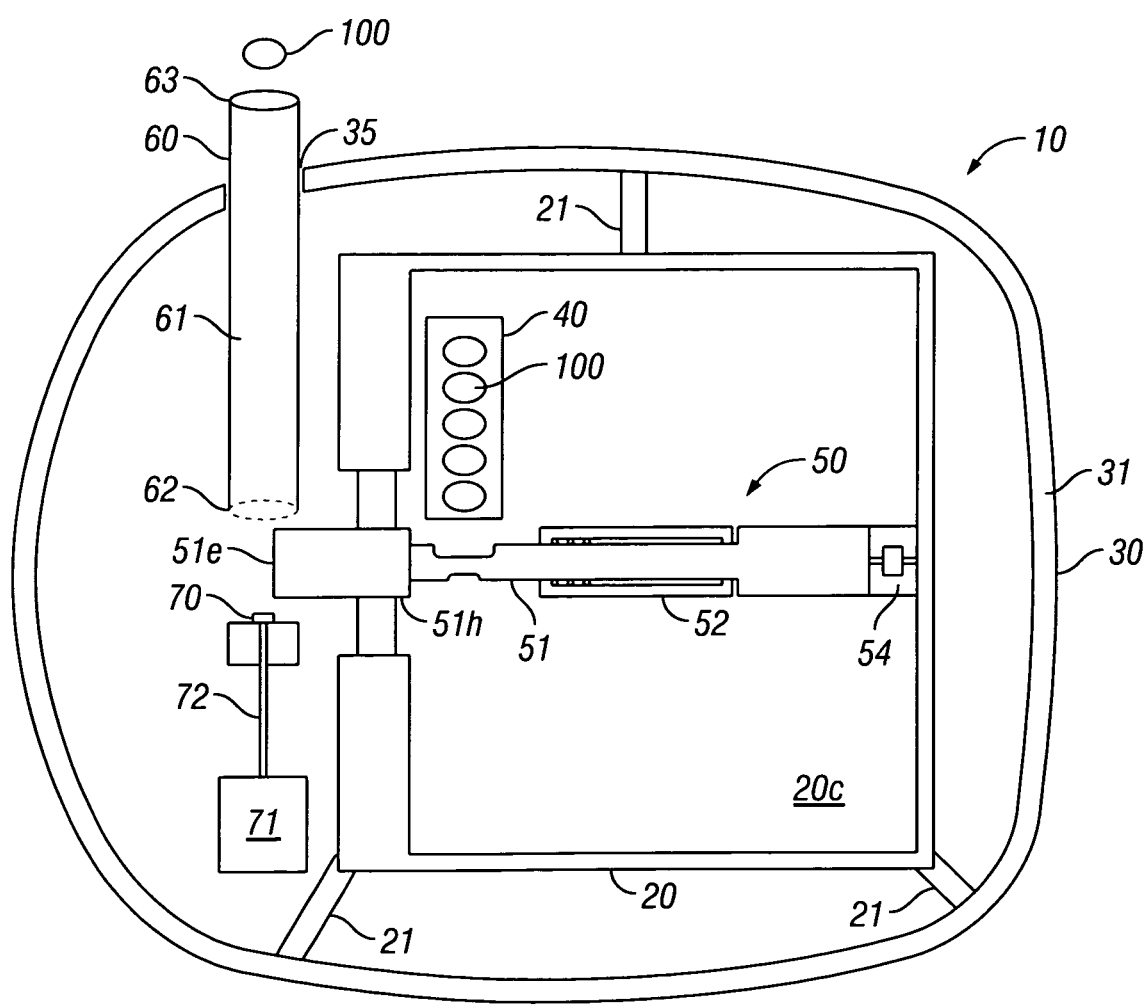
FIG. 1 is a side viewing showing an embodiment of a solid drug delivery apparatus.
Figure 4:
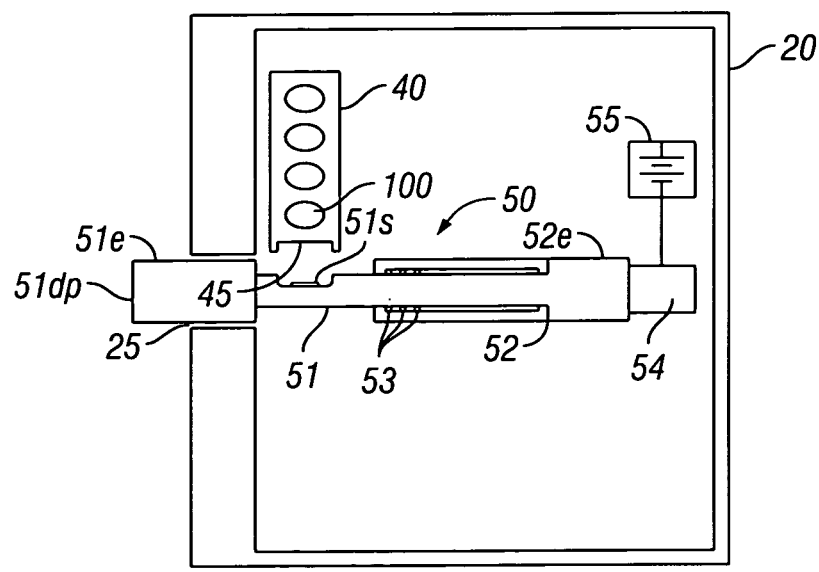
FIG. 4 is a side viewing showing an embodiment of a mechanism for transferring medication pellets between different chambers of the apparatus.
Figure 5A:
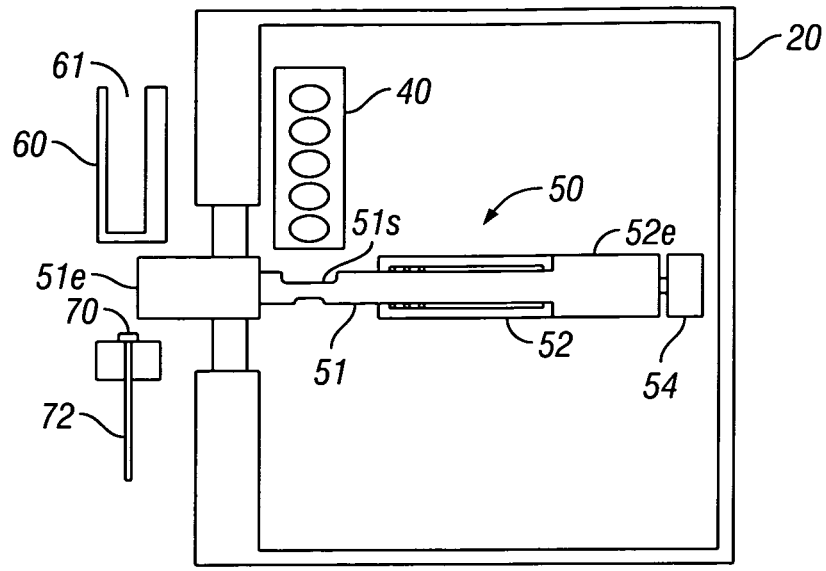
FIGS. 5a-5g are side views showing operation of an embodiment of the transfer mechanism having reciprocating motion.
Figure 5B:
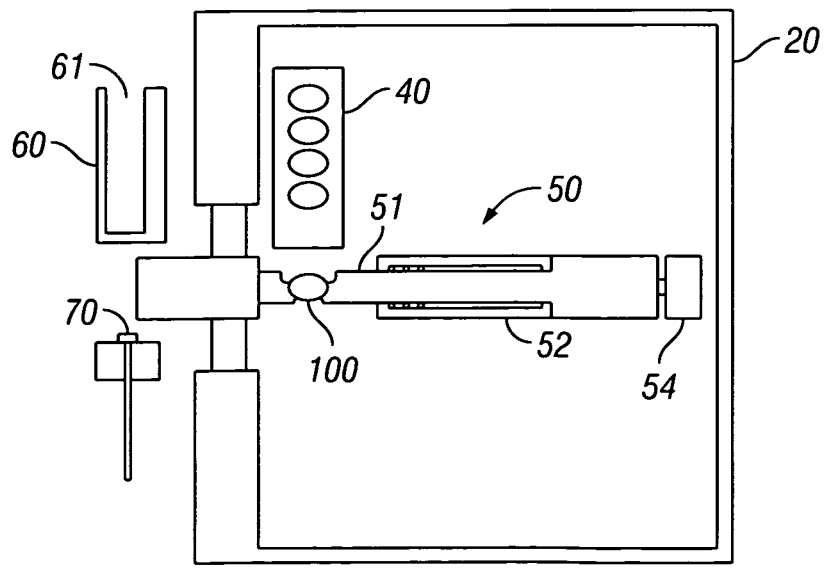
Figure 5C:
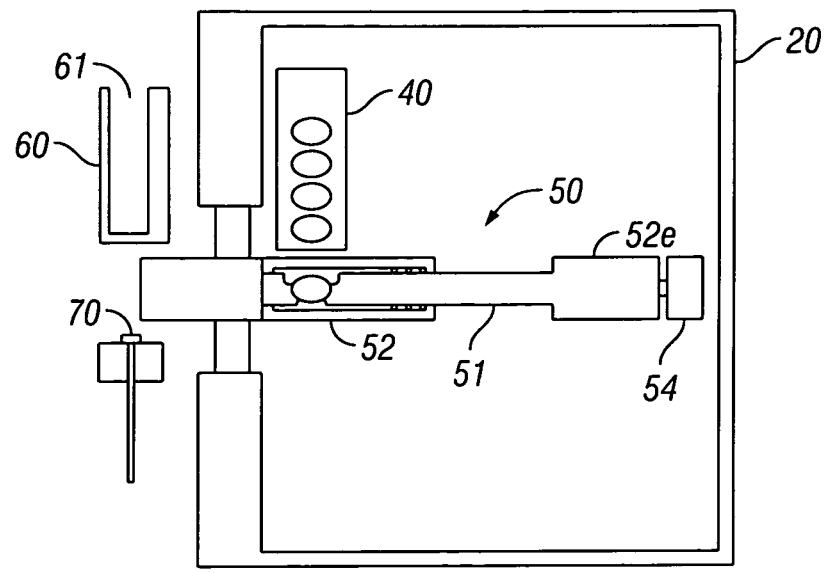
Figure 5D:
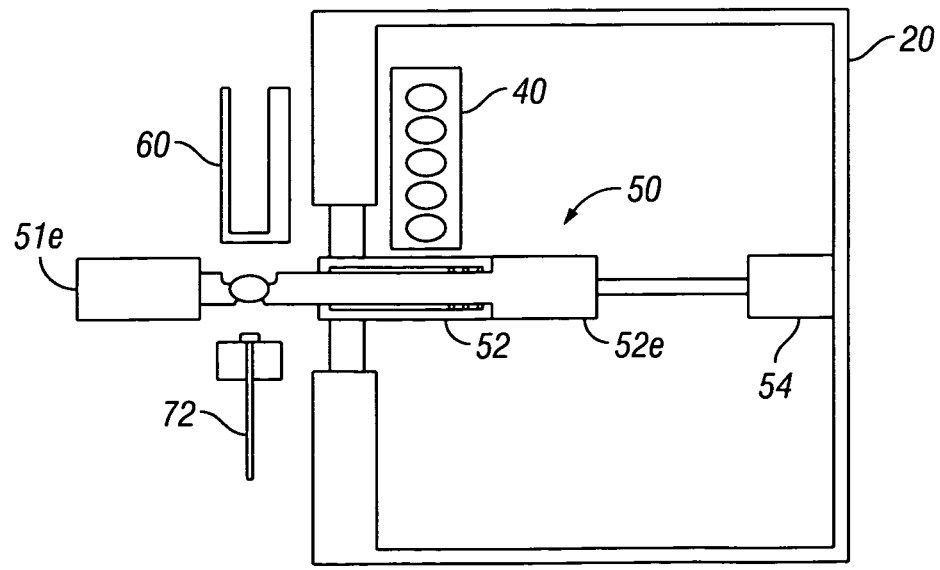
Figure 5E:
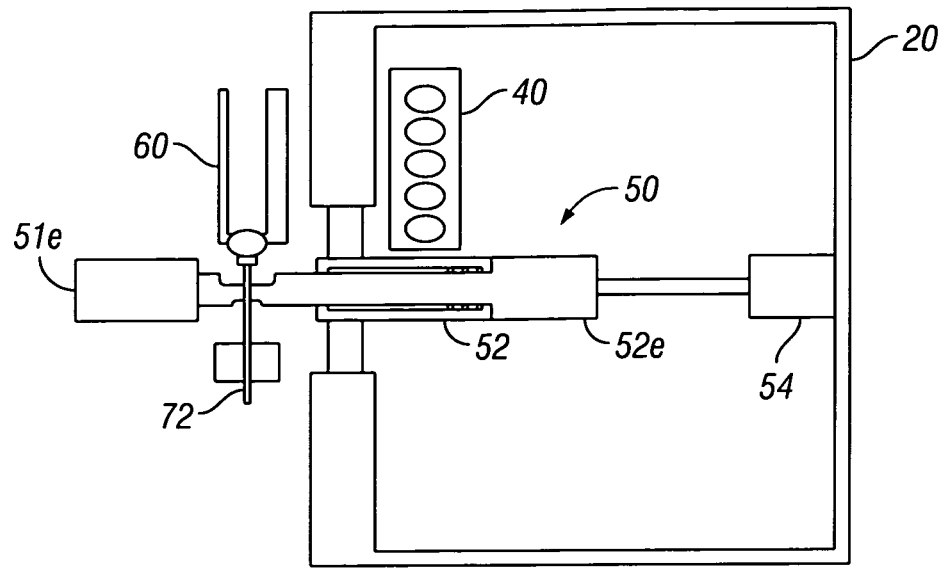
Figure 5F:
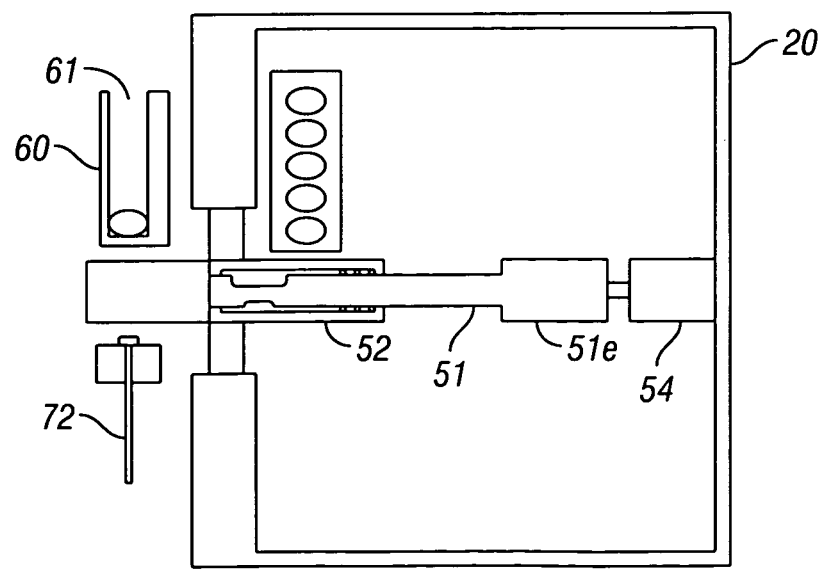
Figure 5G:
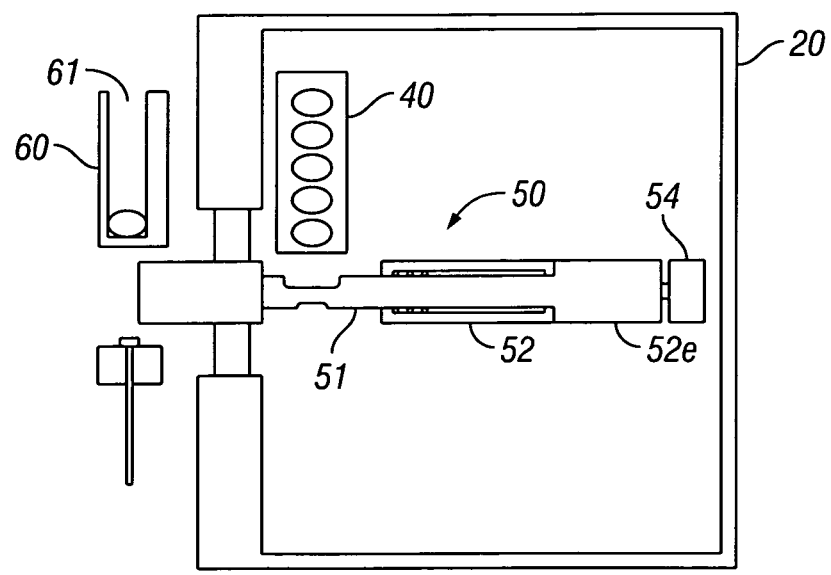

Referring now to FIGS. 1 and 4, an embodiment of an apparatus 10 for the delivery of a solid form medication 100 to a delivery site DS, comprises a first chamber 20 including a first chamber opening or port 25; a second chamber 30 (also known as outer chamber 30) substantially surrounding the first chamber and including a second chamber opening or port 35, a carriage 40 disposed in the first chamber, a mechanism 50 for transferring medication from the first chamber to the second chamber and a pusher plate or other transfer element 70 for transferring solid medication 100 from the second chamber to the exterior of the chamber. As will be discussed herein, in many embodiments, port 35 is coupled to an elongate member 60 such as a catheter 60 having a lumen 61, a proximal end 62 coupled to opening 35 a distal end 63 positioned at a tissue delivery DS for delivery of solid medication 100.

Figure 2A:
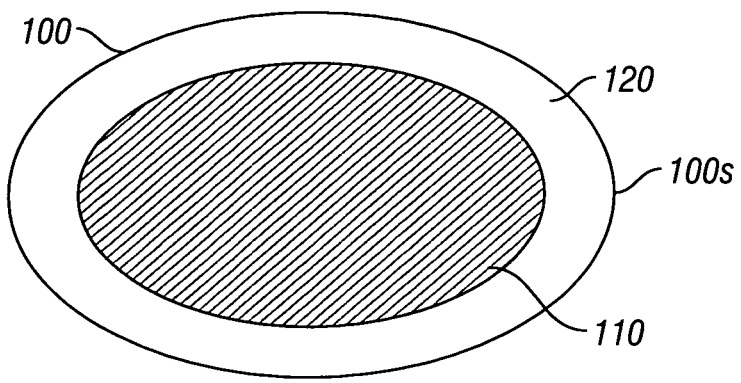
FIG. 2a is a side view illustrating an embodiment of the medication pellet.

Referring now to FIG. 2a, solid form medication also described herein as formulation 100 will typically be formulated into pellets, though other solid formulations are also contemplated, such as powder, granules and the like. For ease of discussion, solid form medication 100 will now be referred to as medication pellets 100 and/or pellets 100, but it will be appreciated that other forms of solid medication 100 are equally applicable. Also as used herein, the term medication comprises a drug 110 or other therapeutic agent 110 and one or more pharmaceutical excipients 120. Other therapeutic agents 110 can include antibodies, vaccines, micro-nutrients and like agents. Accordingly, each pellet 100 contains a selected dose of a drug or other therapeutic agent 110 to treat a particular medical condition such as Furosemide for the treatment of epilepsy. The dose can be selected based on the patient's weight and age. Also in many embodiments, the medication pellets 100 can be formulated using one or more pharmaceutical excipients 120. Suitable excipients 120 include preservatives for preserving the drug, binders for binding the drug components together and disintegrants for disintegrating and dissolving the pellets in a controlled fashion to achieve and maintain a sufficient concentration of the drug (either at the tissue site or other tissue location) for treatment of the condition. As is described herein, disintegrants 120 can include super-disintegrants known in the art. Example super-disintegrants include sodium starch glycolate, crospovidone, croscarmellose sodium as well as related salts and like compounds.

Pellets 100 can have a selectable size and shape 100s and can comprise any number of drugs or other therapeutic agents and can be fabricated using various pharmaceutical manufacturing methods including lyophilization. In particular embodiments, pellets 100 can have a round, oval or other shape. The size and shape of pellet 100 can be selected based upon one or more of the required dose of the drug, the disintegration rate and the delivery site. The shape can also be selected for optimized packing into carriage 40 or other like element. Particular embodiments of pellets 100 can be shaped and sized to allow for packing of 50, 100, 200 or more pellets within carriage 40. The pellets 100 are also desirably fabricated so as to have a shelf life of years when stored in vivo, for example two to five years or longer so that the drug maintain its potency and therapeutic effectiveness. Such shelf lives can be achieved through one or more of the use of preservatives and lyophilization of one or more of the chemical components comprising pellet 100 such that pellets 100 including drugs 110 neither substantially degrade nor suffer other deleterious effects (e.g., effects which reduce the potency or therapeutic efficacy of the drug, for example, wherein the potency or therapeutic efficacy of the drug is reduced by no more than 10, or 1, or 0.1%) while stored in chamber 20. Referring back to FIG. 1, shelf lives can also be facilitated by constructing chamber 20 to have a substantially hermetic seal such that little or no degradation or other deleterious effect occurs to pellet 100 from exposure to moisture, air or other ambient condition which may cause degradation of pellet 100. In specific embodiments, portions of mechanism 50 including section 51e and sleeve 52 can be configured to form a seal 51h which can be maintained during all or a portion of the motion of mechanism 50 through opening 25. Also, one or both of chambers 20 and 30 can include a desiccant such as a Zeolite desiccant to absorb any water vapor that may get into either chamber and/or prevent water vapor from getting into chamber 20. Use of the seal for chamber 20 alone and/or with a desiccant allows the interior 20i of chamber 20 to remain substantially isolated from the environment of the body and thus extend the shelf life of pellets 100.

In various embodiments, pellets 100 can comprise a single or a plurality of drugs 110. In particular embodiments, pellets 100 can include a combination of drugs for treatment of a single or multiple conditions, for example, a cocktail of anti-viral drugs such as protease inhibitors for treatment of HIV AIDS and also antibiotics for the treatment of adjunct bacterial infections.

Figure 2B:
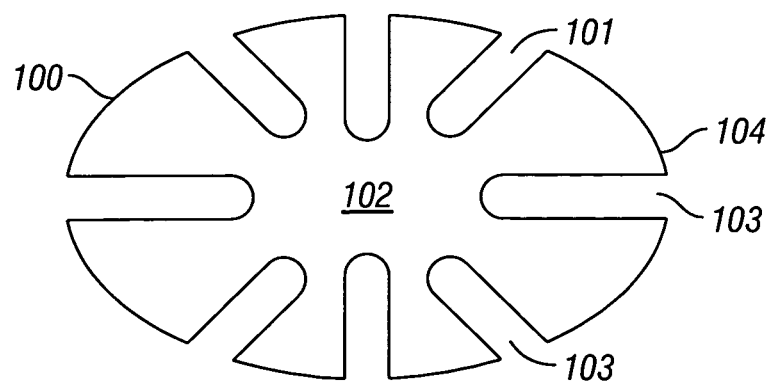
FIG. 2b is a side view illustrating an embodiment of the medication pellet having features for accelerating degradation and dissolution of the pellet by body tissue fluids.
Figure 2C:
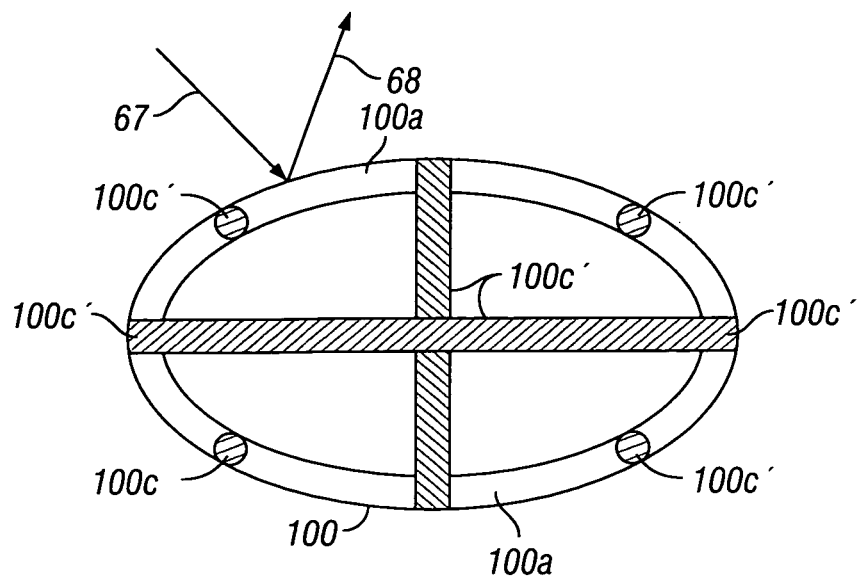
FIG. 2c is a side view illustrating an embodiment of the medication pellet having coatings and optical indicia for measurement of pellet degradation/disintegration by body tissue fluids.

Referring now to FIGS. 2b and 2c, in various embodiments, pellets 100 can include various features and chemical agents to enhance the degradation/disintegration of the pellet as well as quantify the amount and rate of disintegration (as used herein with respect to pellet 100 the terms degrade and disintegrate are essentially interchangeable. In various embodiments, the pellet can be porous or and/or include one or more channels 101 extending inwards from the pellet surface to facilitate the ingress (through capillary action) of body tissue fluids within pellet interior 102 to accelerate disintegration of the pellet by dissolution. In particular embodiments, channels 101 can be arranged in a pattern 103 so as to result in a substantially uniform ingress of body tissue fluids along the pellet circumference 104 as is show in the embodiment of FIG. 2b.

Also in various embodiments, pellets 100 can include echogenic, or optically reflective agents 100a to enhance the reflected an acoustical or optical signal reflected off of pellet 100. As is discussed herein such signals are used to quantify the amount of disintegration of the pellet. The pellet 100 may also include various optical indicia 100i having one or more of a pattern, size or shape configured to provide an indication of the state of disintegration of the pellet. The patterns can be configured to enhance reflectance (optical or acoustic), or contrarily to enhance scattering. Multiple indicia having different patterns (e.g., some reflective some causing scattering) can be positioned at several locations on the pellet. The size and shape of the indicia 100i can be used to determine a total amount of disintegration as well as a rate of disintegration, e.g., the smaller the size of the indicia the more disintegration has occurred with the rate of size decrease of the indicia being correlative to a rate of disintegration. Various calibration measurements may be made (e.g., measuring pellet mass and indicia size over the time course of disintegration) to establish the precise correlative relationship between rate of indicia loss and pellet disintegration (e.g., first order, second order, etc). In particular embodiments, indicia 100i can comprise lines, rectangles, or ovals extending over all or a portion of the length and width of pellet 100 as is shown in the embodiment of FIG. 2b. Other contemplated shapes for indicia 100i include circles and various intersecting shapes such as a criss-cross shape. Indicia 100i may also be placed at various locations along the perimeter 104 of pellet 100.

Referring again to FIGS. 1 and 4, chambers 20 and 30 can be joined by one or more joints 21 which can be mechanical (e.g., a strut, bolt, swage, etc) adhesive or another joining means. Joints 21 can also be flexible allowing outer chamber 30 to twist, bend or pivot with respect to inner chamber 20. One or both chambers can be fabricated from various biocompatible metals and plastics known in the art, such as PET, fluoropolymer, PEBAX, polyurethane, titanium, stainless steel and the like. Also one or both can be fabricated from gas/water vapor impermeable materials or include gas impermeable layers so as to minimize the transmission of water vapor into chamber 20 and/or 30. Suitable gas/water impermeable materials include isobutyl rubbers. Outer chamber 30 can also include one or more biocompatible coatings 31 known in the art including polyurethanes, silicones, fluoropolymers, DACRON and the like. Coating 31 can also include various eluting drugs such as various steroids known in the cardiovascular implant arts for reducing the amount of cellular and other bio-adhesion to the chamber. Outer chamber 30 can be sized and shaped to fit in various locations in the body including the skull and cranial cavity, the chest, within in one or more GI organs, the heart, the vascular system, as well as various subcutaneous and intramuscular locations including the extremities and the trunk. All or portions of chamber 30 can also be constructed from conformable materials (e.g., polyurethane silicone and other elastomeric polymers) to conform to the shape of surrounding tissue layers and compartment, e.g., the curvature on the inside of the skull, or the contour of the skin. Conforming materials can also be employed to allow for surrounding body tissue to grow around and reshape the outer chamber during prolonged periods of implantation. In this way, embodiments having a flexible outer chamber minimize the effect of the chamber on the growth and function of surrounding tissue, thus allowing the apparatus to be implanted over very prolonged periods including allowing the apparatus to be implanted in children and remain through adulthood. Various conformable materials can also be used to facilitate implantation of apparatus 10 using minimally invasive methods. Such materials allow the apparatus including chamber 30 to bend, twist or otherwise conform so as to be inserted through surgical ports and guiding devices and then reassume its shape once positioned at the intended implantation site. In particular embodiments, bending and twisting of chamber 30 can be further facilitated by the use of flexible joints 21 described herein. Chamber 30 can also be sized and shaped to further facilitate implantation by minimally invasive surgical methods. For example, it can have a particular size and shape such as a cylindrical shape to enable it pass through various minimally invasive surgical ports and guiding devices.

Figure 3A:
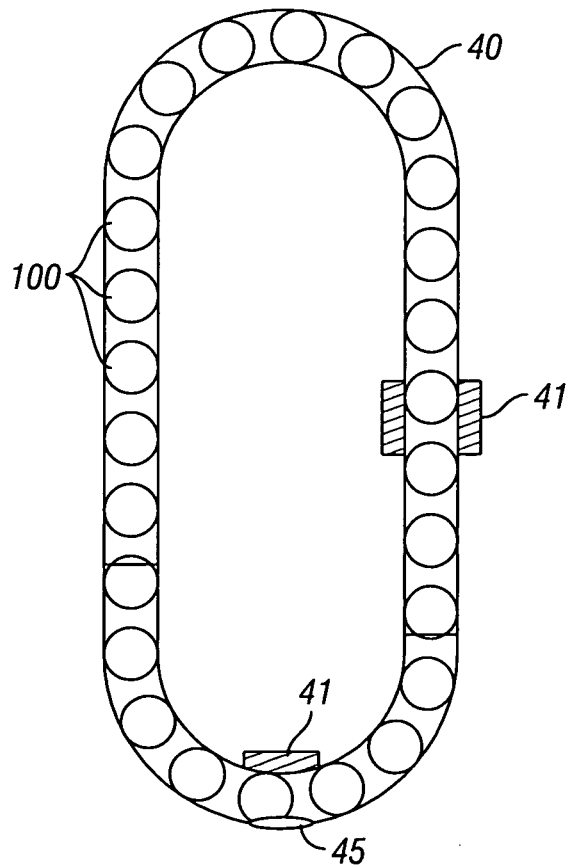
FIG. 3a is a side view showing an embodiment of a carriage for holding a supply of medication pellets.
Figure 3B:
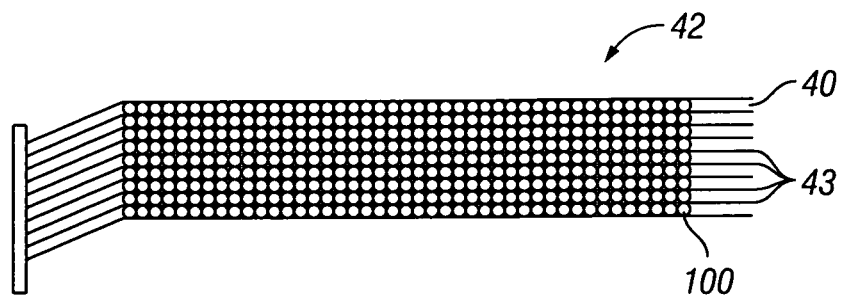
FIG. 3b is a perspective showing an embodiment of stacked carriages for holding a supply of medication pellets.

Referring now to FIGS. 1, 3a and 3b, carriage 40 is configured to hold and dispense a plurality of medication pellets 100 or other solid form medication 100. Typically, this will be through an opening 45 which engages or otherwise provides access to one or more components of mechanism 50 for the component to engage an individual pellet. In one or more embodiments, carriage 40 can be spring loaded to eject pellets 100 for engagement by mechanism 50. In other embodiments, the carriage can also be configured to supply pellets to mechanism 50 by gravity feed or related means. Other pellet ejection means are also contemplated including hydraulic and gas ejection means. Desirably, the carriage 40 contains a sufficient supply of medication pellets to provide treatment of a particular medical condition for an extended period of time, for example, two to five years or longer. In various embodiments, the carriage 40 can be configured to hold up to several hundred or more pellets and may include sensors 41 for determining the number of remaining pellets. The carriage 40 can also be configured to eject or otherwise provide for the delivery of two or more pellets 100 at the same time. Multiple carriages 40 can also be employed in a stacked or other similar fashion so as to comprise stacks 42. FIG. 3b illustrates an embodiment of the invention having a carriage stack 42 comprising two or more stacked carriages 43. Carriages 40 can be stacked in a vertical or horizontal fashion. In such embodiments, the carriage 40 can include one or more mating features (not shown) for connecting one carriage to another. Embodiments having multiple carriages 40 can be configured for delivery of multiple pellets 100 at substantially the same time.

In various embodiments, carriage 40 can be movable or stationary. In many embodiments, it is movable and will typically will be configured to move in a rotary fashion about a central axis, though it may also move in a linear or other fashion. The carriage can be rotated or otherwise advanced through various mechanical or electrical mechanical means such as a spring, an electric motor, a solenoid switch or a piezo-electric drive source. In particular embodiments, the carriage 40 can comprise a rotating or other movable plastic or metal cassette or a belt that engages a drive mechanism (not shown). The drive source can also be built into the carriage, for example in embodiments using a cassette. In such embodiments, various micro machining and MEMs processes can be used to miniaturize the drive source. The carriage can also be configured to remain stationary, such as with embodiments employing gravity feed. In such embodiments, the carriage can comprise a feeder 40.

Carriage 40 can also include one or more sensors 41 that are configured to signal exactly how many pellets 100 are left and/or signal when the pellets have been used up. Sensors 41 will typically also be coupled or otherwise provide inputs to controller 80 described herein. The controller can in turn, can signal this data to an external communication device such as a cell phone, portable monitor or remote monitor (e.g., at the physician's office). In this way, the patient and/or medical care provider can take appropriate action before the apparatus runs out of medication. Typically, sensors 41 will be coupled to carriage 40, but they can be placed at other locations on apparatus 10 as well.

Referring to FIGS. 1, 4 and 5a-5g, a discussion will now be presented of transfer mechanism 50, herein mechanism 50. In many embodiments, mechanism 50 is substantially disposed in first chamber 20 and includes a carrying member 51 configured to receive a medication pellet 100 from the carriage 40, transfer the pellet outside the first chamber through the chamber opening 25 and then return inside first chamber 20. Carrying member 51 will typically include a slot 51s or other opening for holding pellet 100. The distal portion 51dp of the carrying member (that section facing opening 25) can also include an enlarged section 51e which acts as flange to seal against opening 25 and so seal chamber 25 when the sliding member is advanced in an outward (i.e., distal) direction. A sliding member or sleeve 52 can be coaxially or otherwise positioned over the carrying member 51 to hold the pellet 100 in place during movement of the carrying member. Sleeve 52 can have an enlarged section 52e to allow for engagement with various embodiments of a drive source 54 described below. In some embodiments, enlarged section 52e can comprise an independently movable component from the remainder of sleeve 52, allowing sleeve 52 to slide over member 51 to be later followed by section 52e. One or more bearings 53 can be positioned between carrying member 51 and sleeve 52 to allow the sleeve to slide over member 51. The sleeve 52 is configured to be advanced over the carrying member including slot 51s once the pellet is in place in the slot and then move in parallel with carrying element 51 in an outward direction and then move back with the carrying member into chamber 20 and then be retracted to expose slot 51s once the carrying member is completely retracted back into chamber 20. This whole process is repeated each time a new pellet is received from the carriage and advanced out of chamber 20.

One or more components of mechanism 50 including carrying member 51 and sleeve 52 may comprise metal or polymer and can be fabricated using various machining (including micro-machining) and/or molding methods known in the art. Typically, the carrying member 51 and sleeve 52 will be configured to move in a linear manner in and out of chamber 20, though other forms of motion are also contemplated (e.g., rotary motion). Movement of the carrying member 51 and/or the sleeve 52 can be implemented by means of a drive source 54. Drive source 54 can comprise a mechanical drive source such as a spring; or an electro-mechanical drive source such as an electric motor, a solenoid or a piezoelectric motor. In other related embodiments, one or both of carrying member 51 and sliding member 52 can be advanced by means of an electromagnetic force where the members comprise part of an electronic motor such as a linear induction motor.

In many embodiments, the transfer mechanism 50 can be configured to move portions of the mechanism such as the carrying member 51 in and out of the first chamber in a reciprocating motion. FIGS. 5a-5g, illustrate the operation of an embodiment of mechanism 50 having reciprocating motion. In this embodiment, after a pellet 100 is deposited into slot 51s, sleeve 52 advances over member 51 and then distal portions of members 51 and 52 are advanced out of chamber 20, at which point sleeve 52 is withdrawn to expose the pellet, the pellet is engaged and advanced into member 60 by pusher plate 70. Members 51 and 52 are then reciprocally withdrawn back into chamber 20, where member 51 is now ready to receive the next pellet.

The above embodiment employs an electromechanical drive source 54, such as a linear induction motor. However, other drive sources can also be selected and configured to achieve the motion described in the above embodiment. Other suitable drive sources can include spring, magnetic, pneumatic, fluidic and other drive sources known in the art. Embodiments of apparatus 10 having an electro-mechanical drive source 54 can also include a battery 55 or other electric power source for powering drive source 54. Suitable batteries 55 include lithium, lithium-ion, lithium polymer, zinc-air, alkaline and other chemistries known in the electric battery art.

Figure 6A:
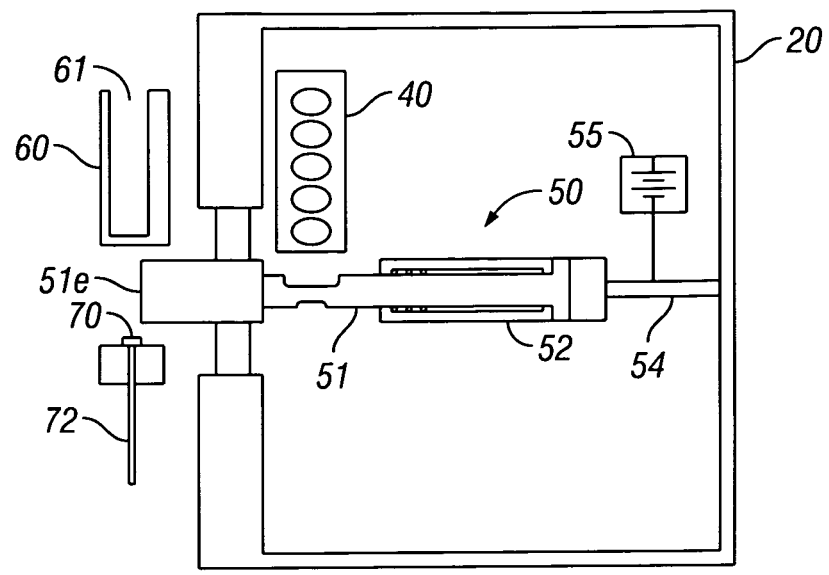
FIGS. 6a and 6b are side views showing operation of a shape memory metal drive source for the transfer mechanism.
Figure 6B:
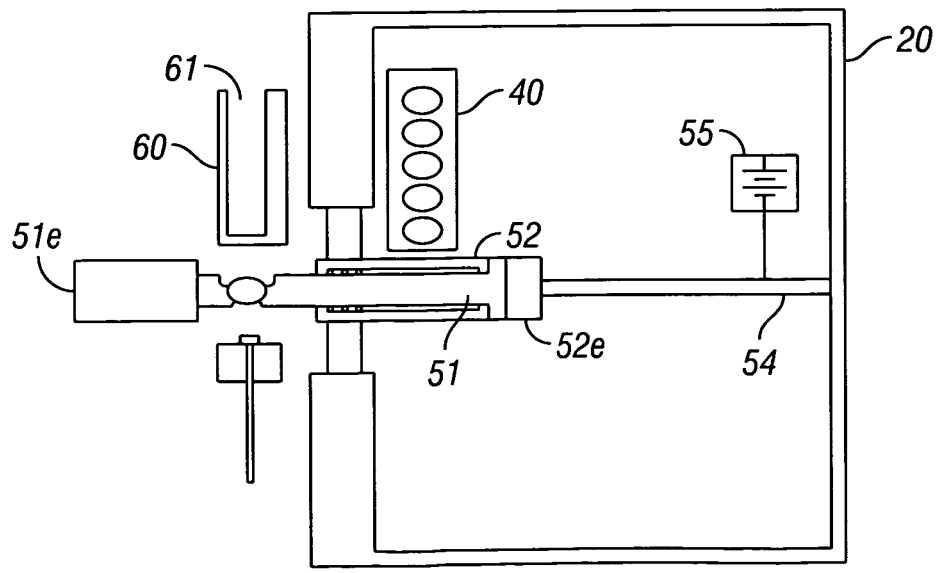
Figure 7A:
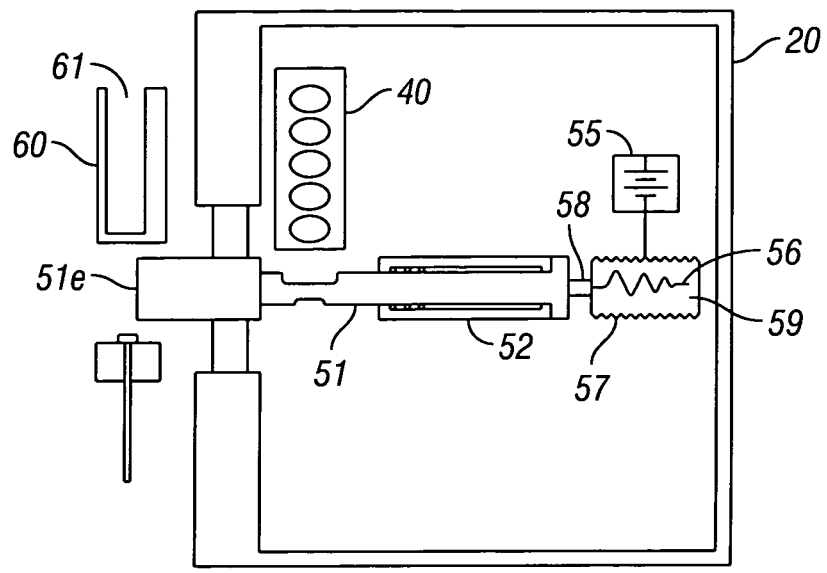
FIGS. 7a and 7b are side views showing operation of a heated gas/piston drive source for the transfer mechanism.
Figure 7B:
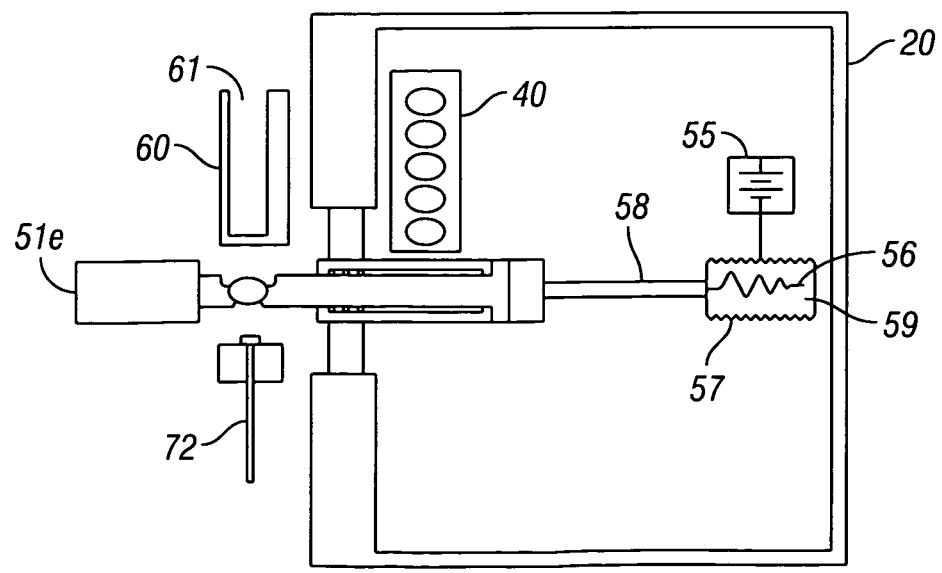

Referring now to FIGS. 6a-6b and 7a-7b, in an embodiment shown in FIGS. 6a and 6b, drive source 54 can comprise a nickel titanium wire or other shape memory material that changes length in response to heating, for example from an electrical current which can be supplied by battery 55 or other electric power source. Use of an expandable gas 59 as a drive source is also contemplated whereby the gas can be expanded by heating from a resistive heating element 56 as is shown in the embodiments of FIGS. 7a and 7b. The gas can be used to expand a bellows 57 which engages one or more of the carrying member 51 or the sliding member 52 by means of a shaft 58 or other connecting member. Shaft 58 can also be used to connect other embodiments of drive source 54 to one or both of sliding member 52 and/or carrying member 51.

Figure 8A:
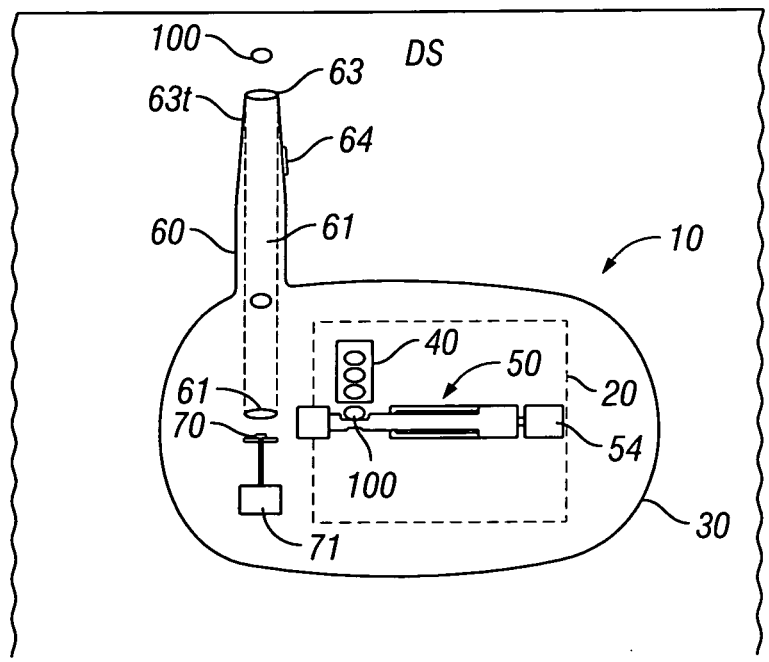
FIG. 8a is a side view illustrating an embodiment of a catheter used to deliver the pellet to the target tissue site.

Referring now to FIG. 8a, in many embodiments, apparatus 10 includes an elongate member 60 attached to outer chamber 30 for delivering a pellet 100 to a target tissue site. Elongate member 60 can comprise a catheter, metal hypotube, or other tubular structure. For ease of discussion, member 60 will be referred to as delivery catheter 60 or catheter 60 but other forms described above are equally applicable. Catheter 60 can be fabricated from various polymeric materials known in the catheter arts including, polyethylene, PET, polyurethanes, silicones and the like. It may also be fabricated from various metallic materials including stainless steel, and various super-elastic metals shape memory materials such as nickel titanium alloys (an example including NITINOL). Catheter 60 has a lumen 61 sized to receive the medication pellet, a proximal end 62 positioned inside chamber 30 or coupled to opening 35 and a distal end or tip 63 that extends outside of chamber 30 to deliver the pellet to a delivery tissue site DS. In particular embodiments catheter 60 can have sufficient length to deliver pellet 100 to a different tissue site than the location of device 10 (for example, into the brain when the rest of apparatus 10 is located outside of the skull). Also in particular embodiments, catheter 60 can be configured to provide the driving force for advancing pellet 100 from chamber 30 to delivery site DS. The driving force can comprise a peristaltic like wave of contraction that travels distally along the length of the catheter. This can be achieved by constructing catheter 60 from either a piezoelectric or like material and coupling it to a voltage source or a shape memory material and coupling it to a thermal power source as is described herein. In the former case, the application of a voltage causes contraction of the catheter material and in the later case the application of heat does so. In an alternative embodiment for transporting pellet 100 through catheter 60, pellet 100 can be charged or include a charged coating, such that the pellet is repelled from the catheter by the application of an electric voltage (having an opposite charge) to the catheter surface or a pusher plate 70 as is described herein.

Desirably, distal catheter tip 63 has an atraumatic configuration to allow for extended periods of implantation at the target delivery site. This can be achieved by configuring the tip to have a tapered shape 63t as well as fabricating the tip from one or more atraumatic flexible polymeric materials including silicones and polyurethanes, fluoropolymers and other known in the art. Catheter 60 including distal tip 63 can also include one or more sensors 64 for making various measurements at the delivery site DS. Such measurements can include drug concentration, pH, glucose, various metabolites, tissue $PO_2$ and $CO_2$ and the like.

Figure 8B:
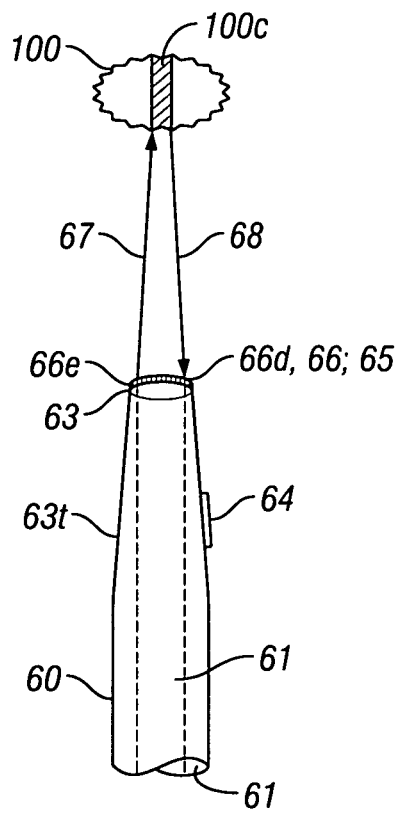
FIG. 8b is a side view illustrating use of an embodiment of a catheter having sensors for measuring the disintegration state of a medication pellet.
Figure 9A:
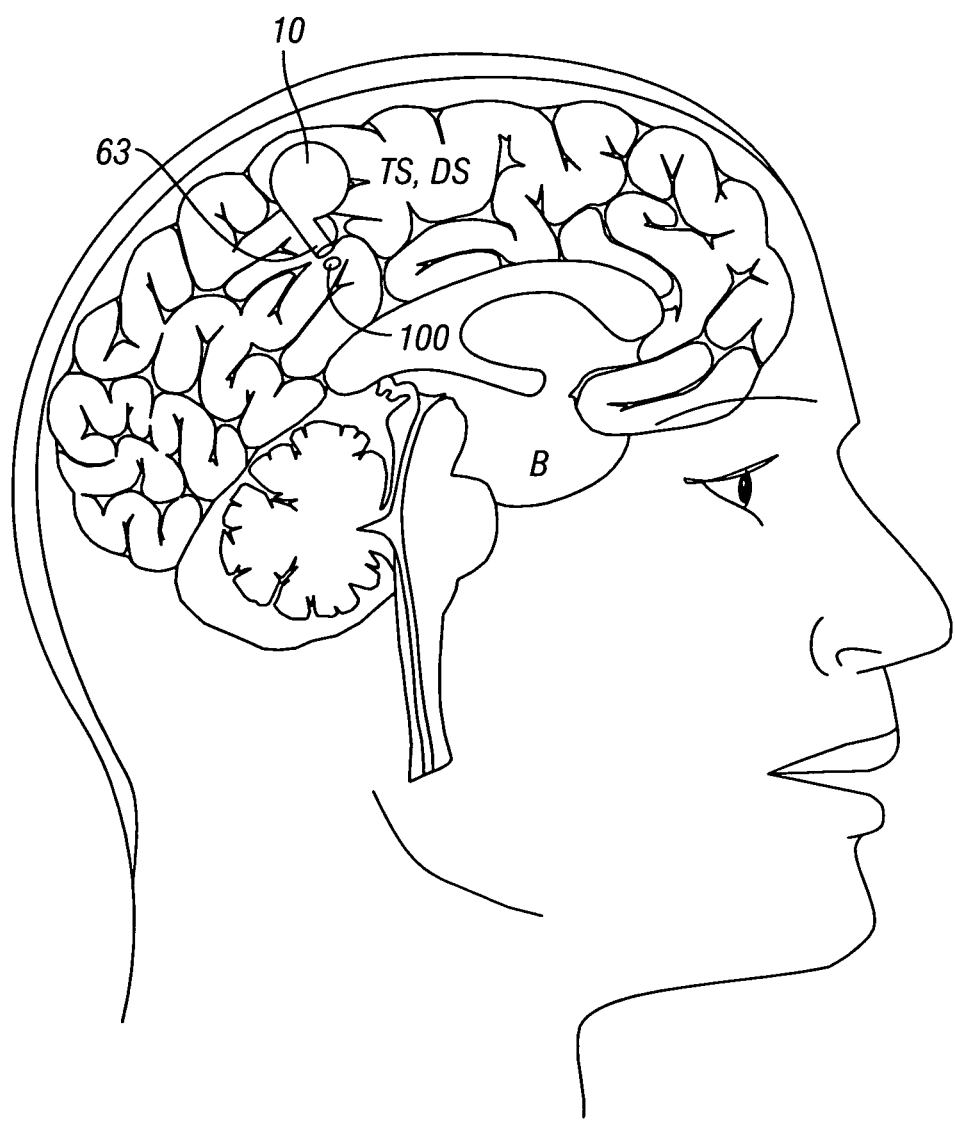
FIGS. 9a-9d show embodiments of the apparatus for placement at different locations in the body.
Figure 9B:
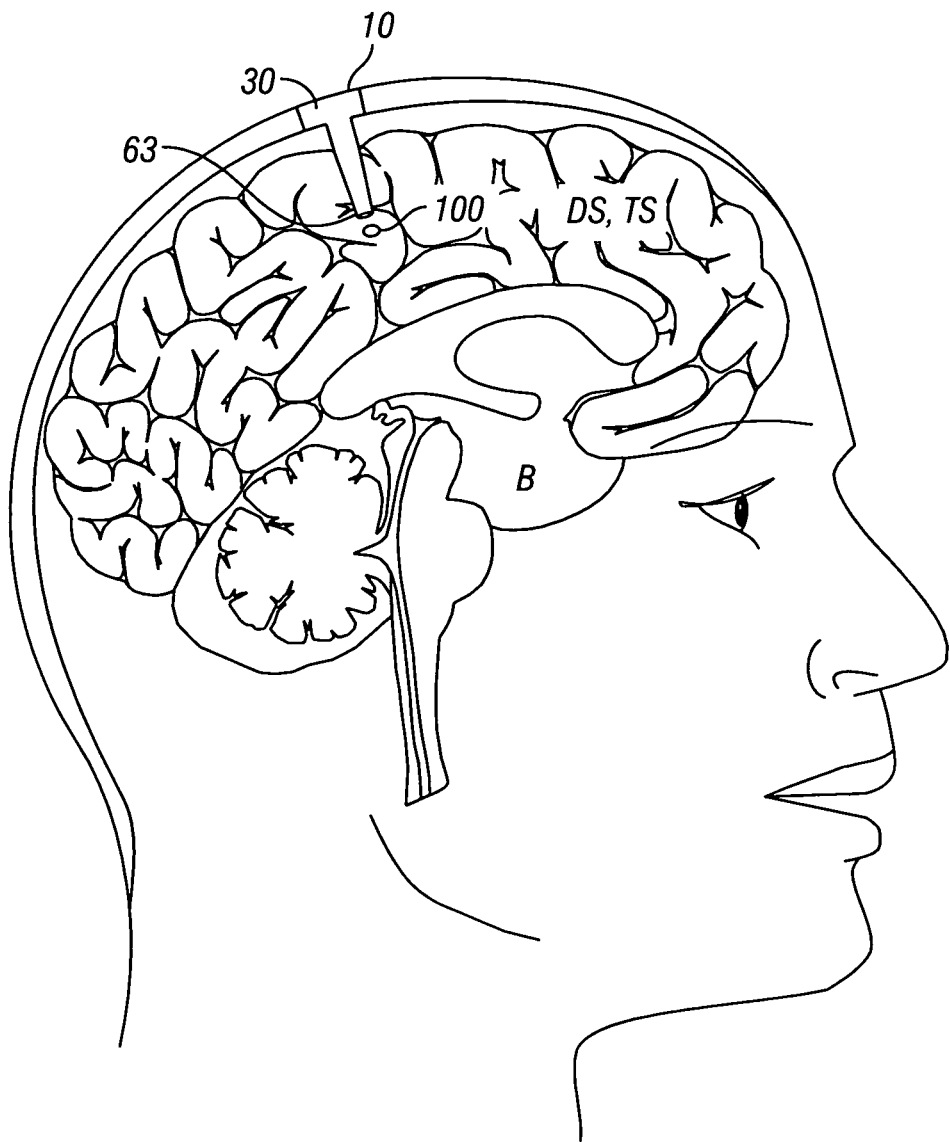
Figure 9C:
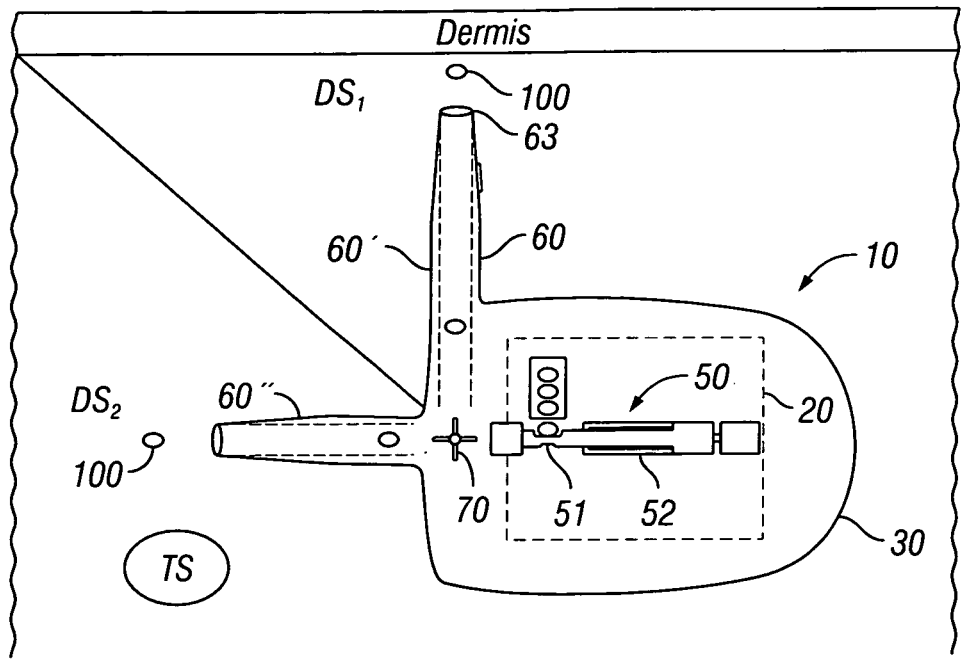
Figure 9D:
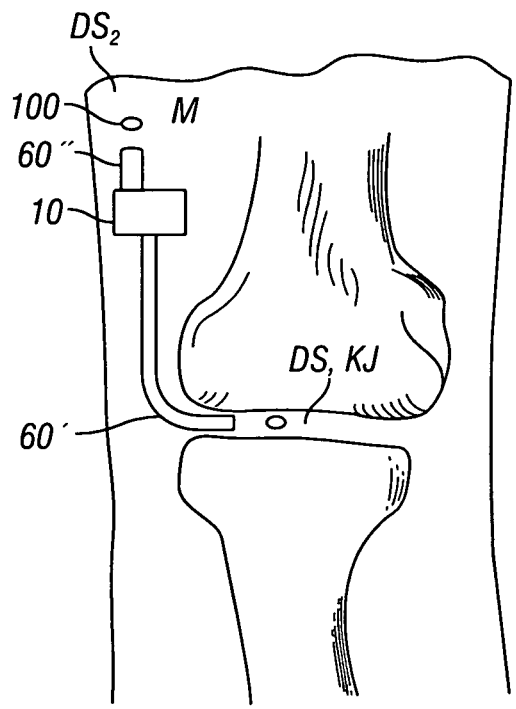

Referring now to FIG. 8b, in particular embodiments, sensor 64 can also comprise sensors 65 for making various measurements for determining the degradation/disintegration state of pellet 100. Suitable sensors 65 for making such measurements can comprise optical, impedance, acoustical and chemical sensors. Sensors 65 can also comprise an assembly 66 including an emitter 66e and detector 66d. Assembly 66 can include optical emitters and detectors for making reflectance measurements and ultrasonic transducers (configured as an emitter and detector) for making ultrasonic measurements. Assembly 66 sends or emits a signal 67 which is modulated or otherwise altered by the degradation/disintegration state of the pellet 100 and then reflected back by pellet 100 as a signal 68 which can then be analyzed to determine the degradation state of the pellet. For example, for use of an optical based assembly 66, signal 67 will be returned as a reflected signal 68 which progressively decreases in amplitude as the pellet is dissolved and disintegrated by body tissue fluids. As indicated above, in various embodiments, pellet 100 can include optical indicia 100i to facilitate measurement of the degradation state of pellet 100.

Embodiments having sensors 65 and 66 can be used to control or regulate pellet delivery by sensing the state of disintegration of previously delivered pellets. For example, another pellet can be delivered when it has been determined that the previous pellet is in a particular state of disintegration (e.g., it has been completely or substantially disintegrated). This determination can be achieved through use of a controller 80 described herein which may include one or more algorithms for analyzing the disintegration state of the pellet and using this information to make a delivery decision. In particular embodiments, information on the disintegration state of the pellet can be combined with other data for making a pellet delivery decision with weightings assignable to each group of data. Such additional data can include the blood concentration of the drug as well as various physiological data (e.g., temperature, pH, blood gases, etc) including physiological data indicative of the medical condition to be treated by the delivered drug, e.g., blood glucose as an indication of hyperglycemia, EKG as an indication of arrhythmia or brain electrical activity as an indication of an epileptic seizure or pre seizure event.

Referring now to FIGS. 9a-9d, the length of the catheter 60 can be configured to allow the apparatus 10 to be positioned near the delivery site DS or to be positioned at a different location. For example, in one embodiment shown in FIG. 9a, apparatus 10 can be positioned in the brain B with the catheter tip 63 positioned a short distance away. In another embodiment shown in FIG. 9b, the catheter can have sufficient length to allow distal tip 63 to be positioned in the brain, while apparatus 10 is placed on the scalp or other location outside the skull.

In some embodiments, apparatus 10 can include multiple catheters 60 so as to allow for the delivery medication pellets 100 at multiple locations using a single delivery apparatus 10. For example, in an embodiment shown in FIG. 9c, the distal tip 63 of a first catheter 60' can be placed at first delivery site DS1 and the distal tip 63 of a second catheter 60" can be placed a second delivery site DS2. In an embodiment shown in FIG. 9d, the first delivery site DS1 can comprise the ultimate target site TS such as an arthritic knee joint KJ (or other arthritic joint) to allow for immediate delivery of medication to that site and the second catheter distal tip can be placed at a second site DS2 at least partially removed from first site DS1 such as in muscle tissue M or other sub-dermal location to allow for longer term controlled release of the drug.

Referring now to FIGS. 10a-10d, pusher plate 70 is used disengage the pellet 100 from the mechanism 50 and push or advance the pellet into the catheter lumen 61 and out to the delivery site DS. In one embodiment, pusher plate 70 can be coupled to a drive source 71 via a shaft 72. In another embodiment, it may also be coupled to one or more drive source 54 described herein. In a particular embodiment pusher plate 70 can comprise a piezo-electric plate that is mechanically actuable through use of voltage from power source 55. As an alternative to pusher plate 70 or in combination with it, other pellet advancement means can include use of a liquid coupled to a miniature pump (not shown) which develops sufficient pressure for the liquid to carry the pellet out of the elongate member. The liquid can be taken from a reservoir (not shown) or in some embodiments can be drawn from the body itself (e.g., from interstitial fluid, or blood in the surrounding delivery drawn in through catheter 60 or a separate inlet catheter not shown) via means of a miniature peristaltic pump which never makes direct contact with the liquid. For embodiments using catheter 60 as an inlet, the pump can be configured to pump in an inward direction to draw in the fluid for discharging the pellet, and then in an outward direction for discharging or ejecting the pellet into the delivery site. One or more valves can be positioned in the proximal portions of catheter 60 to facilitate this process. Such embodiments can be used in combinations with pusher plate 70 where the pusher plate advances pellet 100 into the catheter 60 and then the pressurized liquid is used to advance the pellet out of the catheter.

Figure 10A:
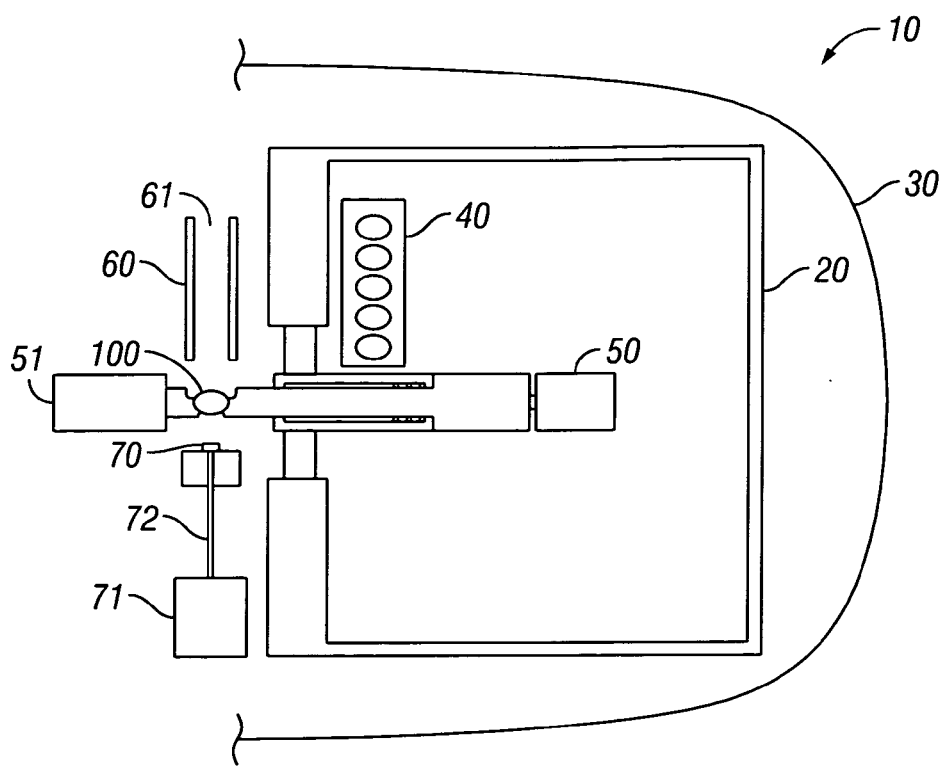
FIGS. 10a-10d are side views illustrating operation of an embodiment of the pusher plate to engage and advance the medication pellet.
Figure 10B:
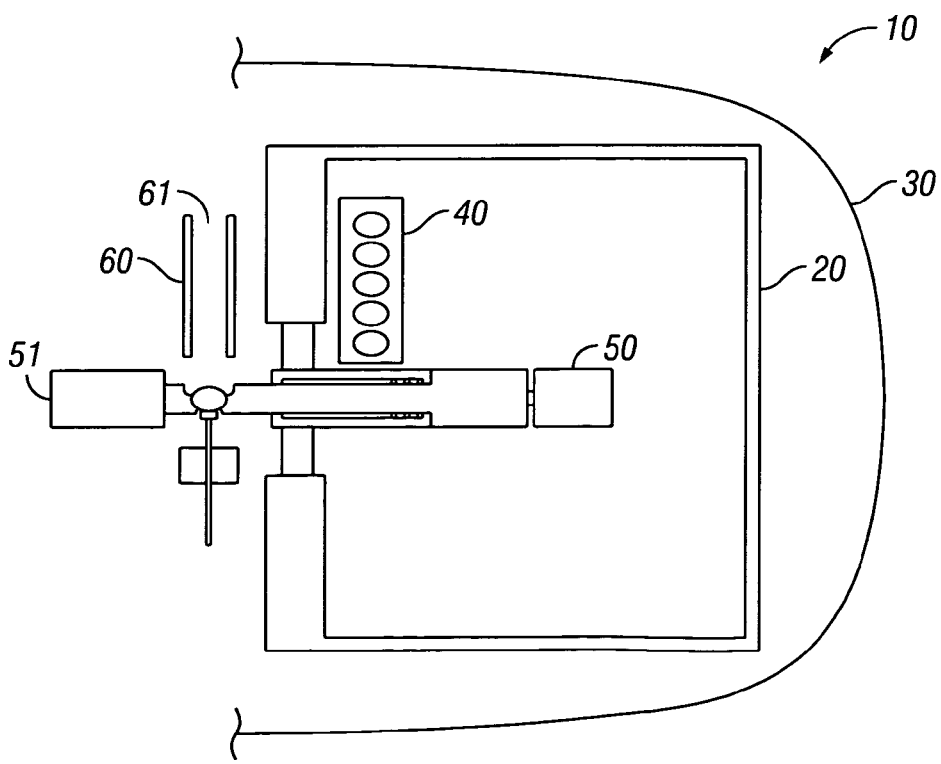
Figure 10C:
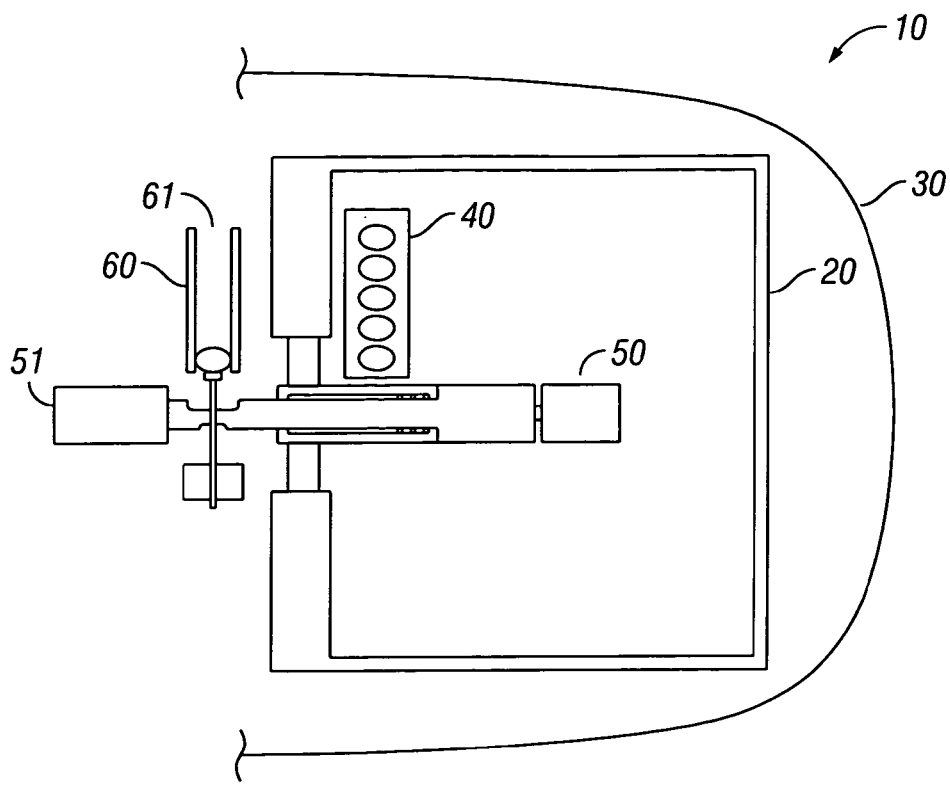
Figure 10D:
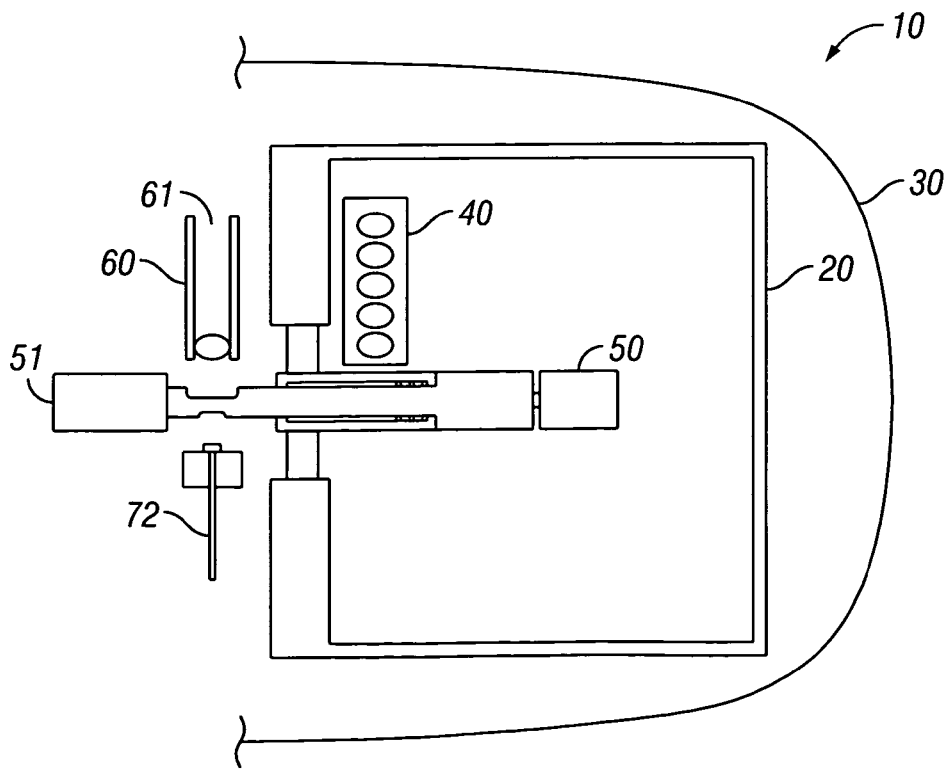
Figure 10E:
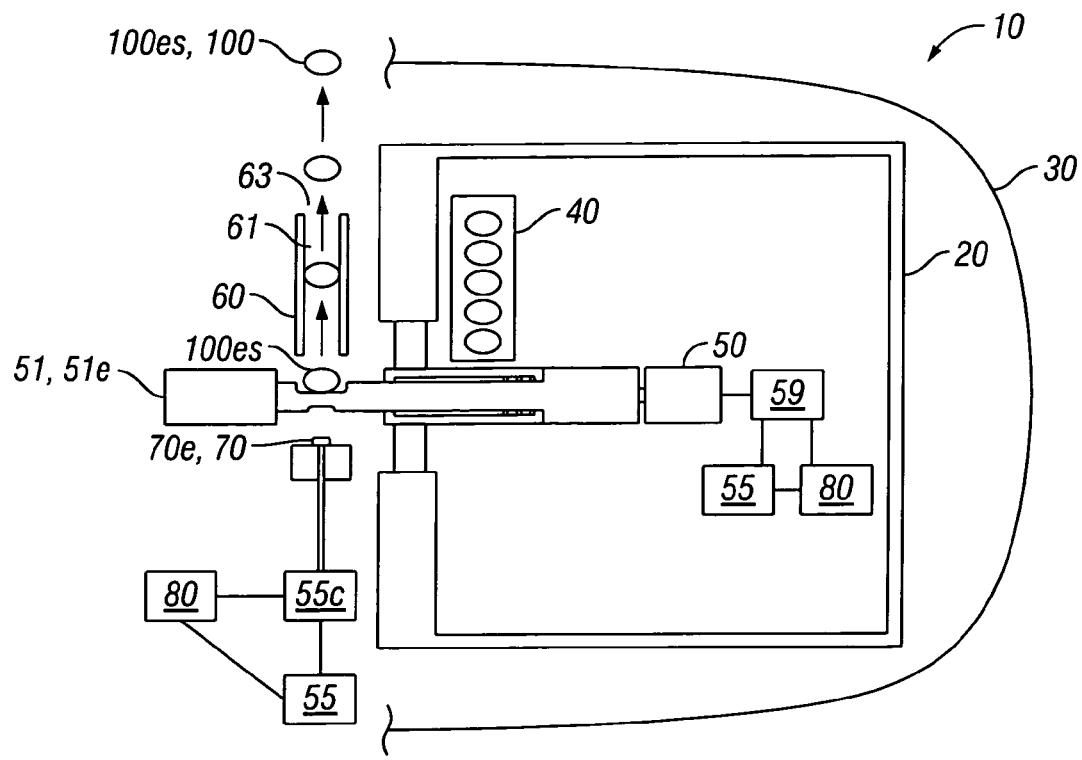
FIG. 10e is a side view illustrating operation of an embodiment of a charged pusher plate to engage and advance the medication pellet.

In still other alternative embodiments, pusher plate 70 can use electromotive force to manipulate pellet 100. Referring now to FIG. 10e, in specific embodiments, pusher plate 70 can use an electromagnetic attractive force to engage pellet 100 from carrier member 51 and an electromagnetic repulsive force to advance pellet 100 out of catheter or other elongate member 60. This can be achieved by imparting an electrostatic charge 100es to pellet 100 using charging circuitry coupled to power source 54 and coupling pusher plate 70 to electrical power source 54 so that plate 70 functions as an electrode 70e with the same polarity as the charge on pellet 100 and then changing the polarity (using circuitry within controller 80) to repel the pellet from plate 70 with sufficient electromotive force to advance the pellet out of catheter 60. This process can be facilitated by filling catheter 60 with saline or other conductive solution which acts to conduct the repulsive charge from plate 70 through all or a portion of catheter lumen 61. In this way, the entire lumen of catheter 60 can function as a repulsive electrode to increase the repulsive forces for ejecting pellet 100 from catheter 60 and thus place the pellet at greater distances in the delivery site from catheter distal tip 63. The charge on pellet 100 can be achieved by coating the pellet with an electrically insulating material so that it holds a charge on its surface. In an alternative approach for applying a charge on pellet 100, the pellet can include a permanently charged coating such as a coating comprising one or more ionic species (phosphate, sulfate and like groups) which are covalently bound to the surface of the pellet. The amount of repulsive force applied to pellet 100, can be controlled by the amount of voltage applied to plate 70 from power source 54. The amount of voltage can be controlled through various power control circuitry 55c coupled or resident within controller 80 such as a dc-dc converter or dc-ac converter.

Figure 11:
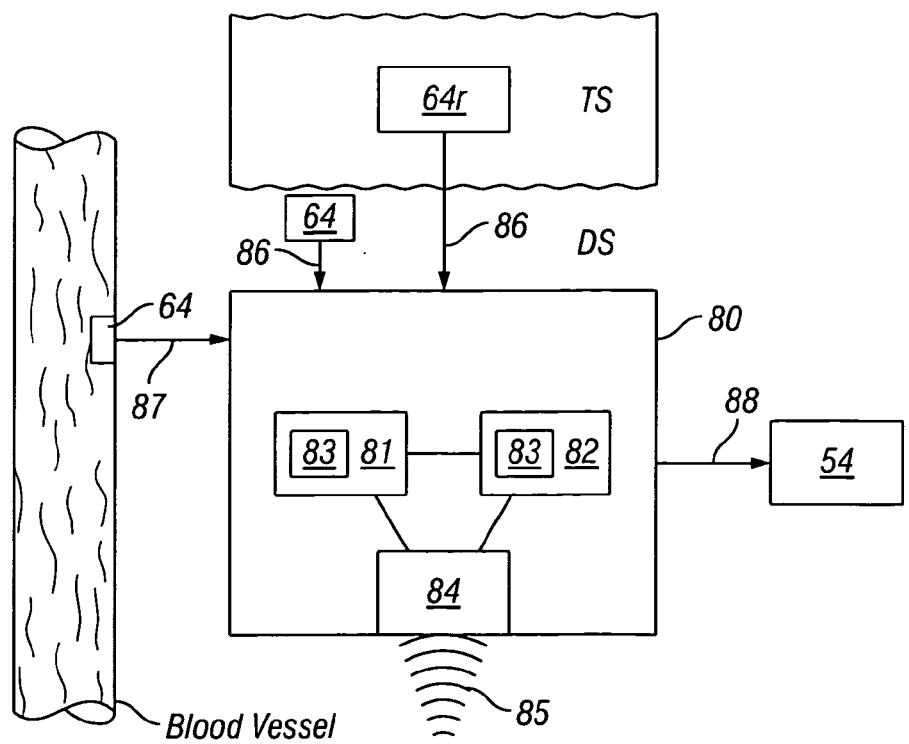
FIG. 11 is a schematic block diagram illustrating an embodiment of a controller for use with one or more embodiments of the solid drug delivery apparatus.

Referring now to FIG. 11, in many embodiments, apparatus 10 can include a controller 80 for controlling one or more aspects of the medication delivery process including actuation and control of mechanism 60. The controller can comprise logic resources 81 such as a microprocessor, a state device or both; and memory resources 82 such as RAM, DRAM, ROM, etc. Logic resources 81 and/or memory resources 82 may include one or more software modules 83 for operation of the controller 83. Through the use of modules 83, the controller 80 may be programmed to include a medication delivery regimen wherein medication is delivered at regular intervals (e.g., once or twice a day, etc) over an extended period. The controller may also include an RF device 84 for receiving a wireless 85 signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of angina) or longer term changes in the patient's condition or diagnosis.

The controller 80 can receive inputs 86 from apparatus sensor 64 or a remote sensor 64r which senses a physiologic parameter indicative of a condition to be treated by the medication pellet 100, e.g., diabetic hyperglycemia. When the controller 80 receives an input 86 indicative of the condition, it sends a signal 88 to initiate the delivery of one or more medication pellets 100 to the target tissue site so as to treat the medical condition. Both the initial and subsequent inputs from sensor 64 can be used to titrate the delivery of medication pellets over an extended period until the condition is dissipated or otherwise treated in a selected manner. The controller 80 can also receive inputs 87 from other sensors 69 which are configured to measure the plasma or other tissue concentration of the delivered drug. These inputs 87 can also be used to titrate the delivery of the drug to achieve a selected concentration of drug. The concentration sensors 69 can be positioned both at the delivery site DS, the target site TS as well as other sites in the body (e.g., a vein or artery) in order to develop a pharmacokinetic model of the distribution of the drug at multiple sites in the body.

Figure 12A:
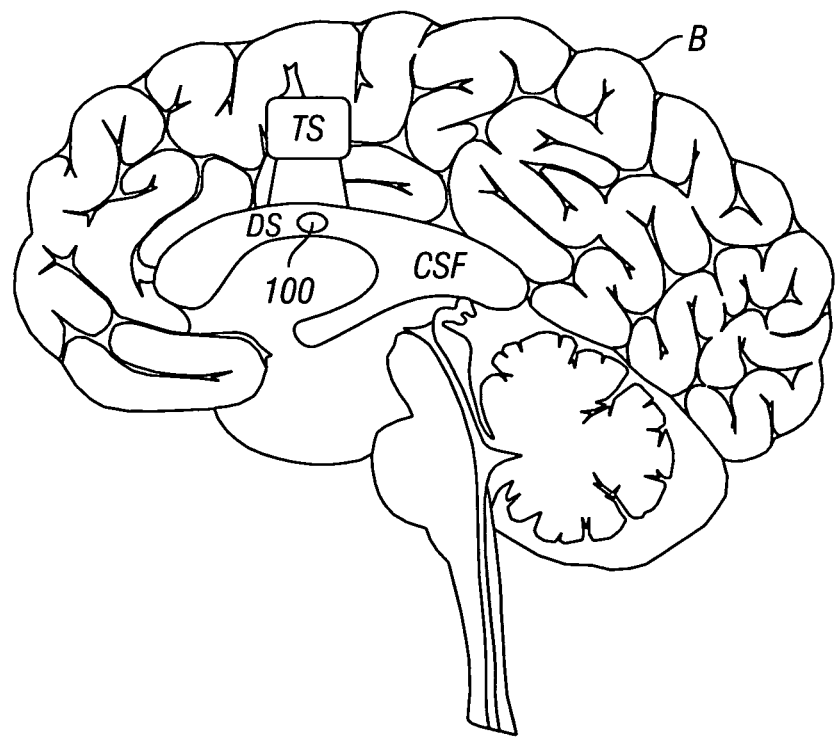
FIG. 12a shows placement of a medication pellet in a ventricle brain for dissolution and delivery of the drug to a target site in the brain.
Figure 12B:
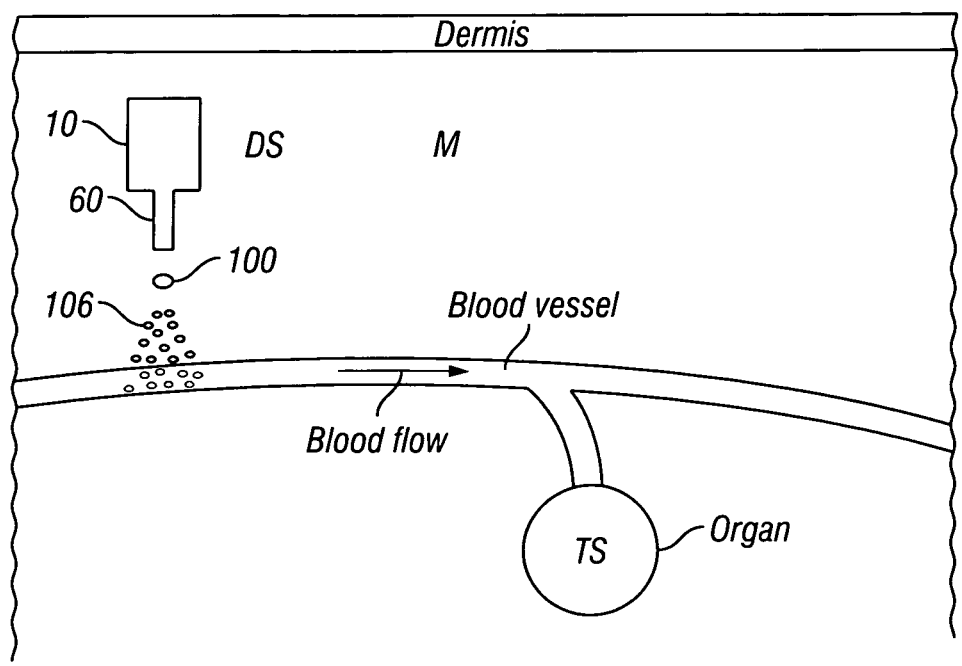
FIG. 12b shows placement of a medication/drug pellet at a delivery site for transport of the drug to a target tissue site removed from the delivery site.
Figure 13A:
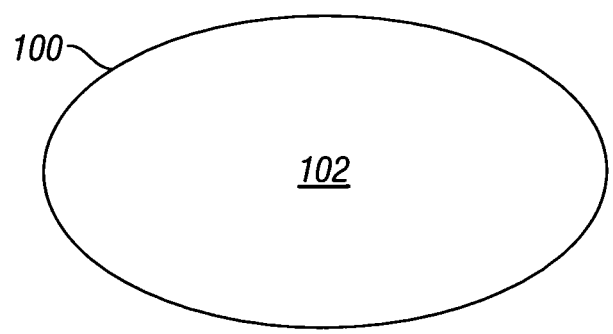
FIGS. 13a and 13b are side views of the pellet illustrating the delivery of force or energy to break down the pellet structure so as to enhance dissolution of the pellet.
Figure 13B:
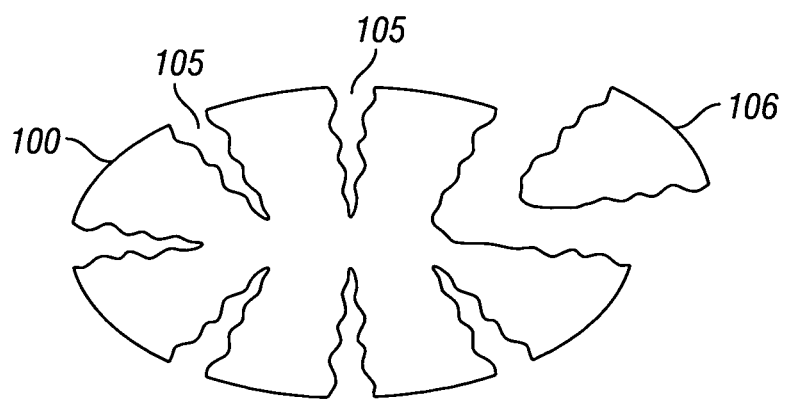

In various method embodiments of the invention, apparatus 10 is used to deliver pellets or other solid form medication 100 to a selected delivery site DS such as subcutaneous tissue where they are disintegrated and absorbed by body tissue fluids (e.g., interstitial fluids in muscle or dermal tissue) so as to produce a desired concentration of drug 110 at a target site TS. In some applications, the delivery site DS can be in the same organ and/or compartment as the target site TS, for example the brain as is shown in the embodiment of FIG. 12a. In others, the target site can be different from the delivery site as is shown in the embodiment of FIG. 12b. For example in one embodiment, the delivery site can be intramuscular tissue in the chest and the target site can be an organ such as the heart which is removed from the delivery site. The delivery site can be oppositional to the target site, for example dermal delivery to reach the target site of underlying muscle tissue, or it can be placed at a non-oppositional site, for example, intramuscular delivery to reach the target site of the heart. In each case, the medication pellet 100 can include a selected dose of drug and be configured to disintegrate and be dissolved by body tissue fluids so as to yield a therapeutically effective concentration of the drug at the target tissue site. In many applications, this involves the pellet being dissolved by body tissue fluids at the delivery site (e.g., interstitial fluids) where the drug then diffuses from the tissue into the blood stream where it is carried to the target tissue site. Accordingly, in these and other applications, the dose of the drug in the pellet can be titrated to achieve a selected plasma concentration of the drug (or concentration range) for a selected period during and after dissolution of the pellet.

In some embodiments, pellet 100 is configured to disintegrate and be dissolved by the tissue fluids within a body compartment such as the cerebrospinal fluid (CSF) in the brain so as to achieve a selected concentration in the tissue fluid within that compartment as is shown in the embodiment of FIG. 12a. In particular embodiments for treating various neural disorders such as epileptic and other seizures, the pellet is configured to rapidly disintegrate and be dissolved in the CSF so as to rapidly achieve a selected concentration of the drug throughout the CSF that bathes the brain in order to prevent the occurrence of the seizure or lessen its duration and severity. This can be achieved through the use of one or more super-disintegrants which are compounded into pellet 100.

Figure 14:
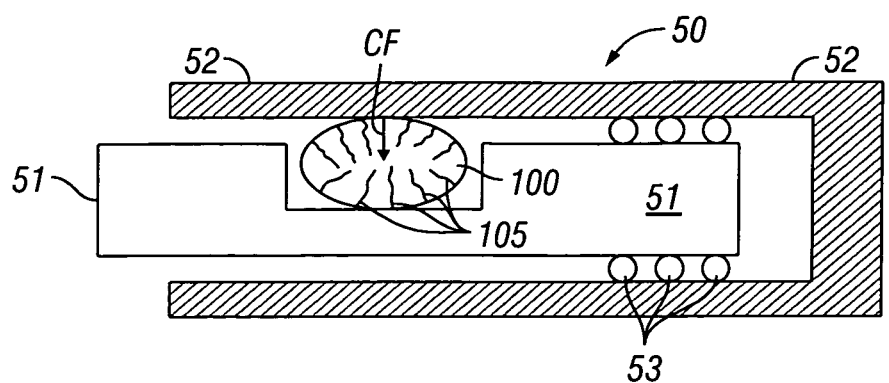
FIG. 14 is a side view illustrating the delivery of a mechanical force to the medication pellet to enhance dissolution of the pellet.

Referring now to FIGS. 13-16, accelerated pellet disintegration can also be achieved by treating the pellet prior to or after delivery with mechanical, electromagnetic, acoustical or other energy to weaken the pellet structure, create cracks for the ingress of fluids or initiate the breakup of the pellet into smaller pieces. As is shown in FIGS. 13a-13b, the delivery of force and energy can be used to create cracks 105 (or other surface defects) for the ingress of tissue fluids as well as break the pellet up into smaller pieces 106. In one embodiment this can be achieved from a mechanical compressive force CF applied by the carrying member and/or sleeve 52 as is shown in the embodiment of FIG. 14.

Figure 15:
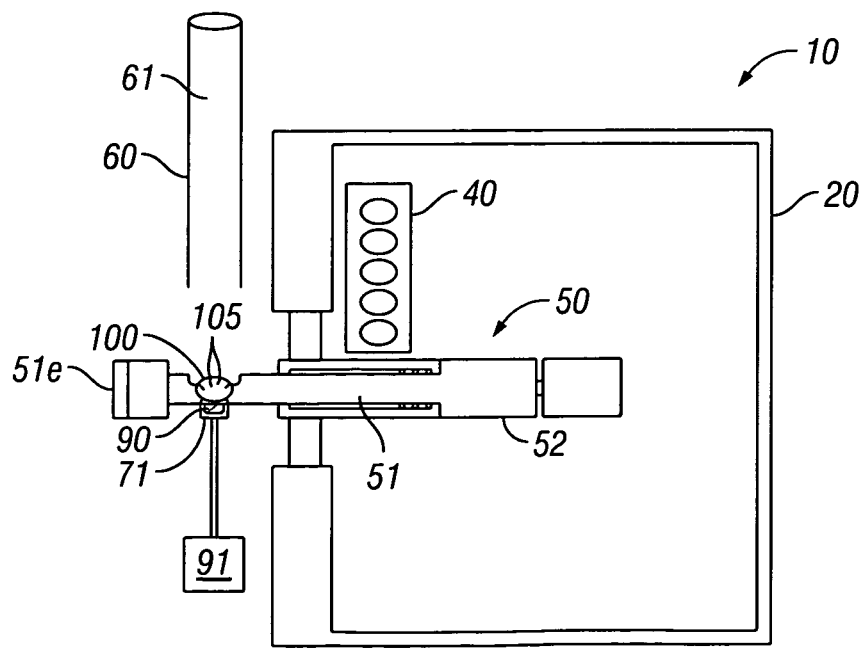
FIG. 15 is a side view illustrating the delivery of energy to the medication pellet prior to delivery to enhance dissolution of the pellet.
Figure 16:
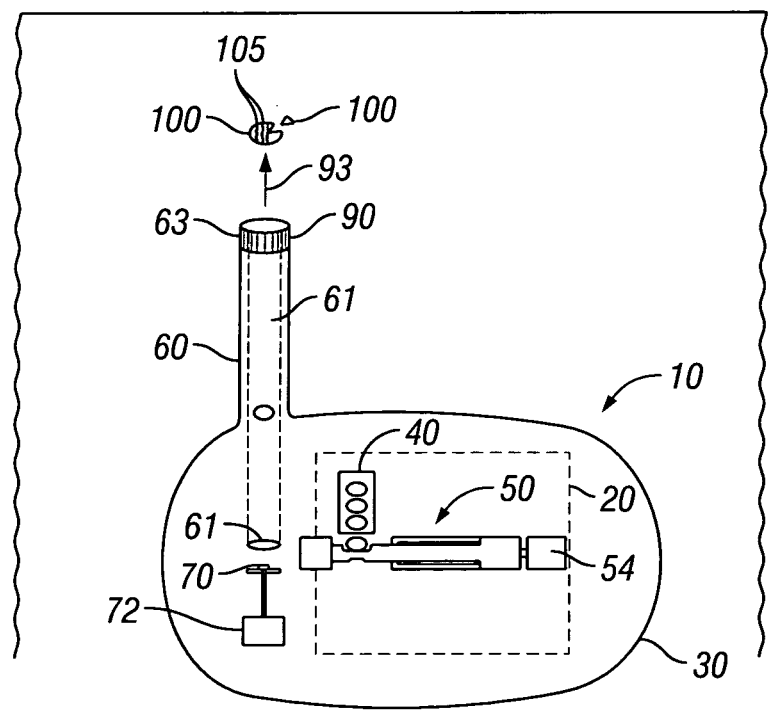
FIG. 16 is a side view illustrating the delivery of energy to the pellet delivery site to enhance to dissolution of pellet.

In other embodiments, energy can be delivered to the pellet 100 while it is still in the apparatus 10 to create cracks 105 and weaken the pellet structure as is shown in FIG. 15. Energy delivery can be achieved through use of an acoustical energy device 90 such as an ultrasonic transducer with the ultrasonic frequency configured for a resonant frequency of the pellet. Acoustical or other energy device 90 can be coupled to an energy source 91, which can include various electrical power sources. In another embodiment shown in FIG. 16, energy can be delivered to the pellet after it is ejected from catheter 60 and delivered to delivery site DS. In this embodiment, energy delivery can be achieved through use of an ultrasonic transducer or other energy delivery device 90 placed on catheter distal tip 63. Ultrasonic transducer 90 emits a beam of energy 93 which acts upon pellet 100 to cause cracks 105 and other effects to the pellet structure to accelerate pellet degradation into pieces 106 and disintegration through dissolution by body tissue fluids. Other forms of energy which can be used to break up the structure of pellet 100 and accelerate disintegration/degradation include optical (e.g., laser), RF, microwave, thermal or other forms of energy known in the medical device arts. The energy delivery regimen (e.g., duration, frequency and amount of energy) for weakening the pellet structure (e.g., causing cracks etc.) can be controlled by controller 80. The energy delivery regimen can be adjusted depending upon the size and structure properties of the pellet as well as the particular delivery site DS. In various embodiments, energy delivery device 90 can be powered by power source 54 or have its own power source.

In various applications, embodiments of the invention can be used to deliver pellets 100 or solid form medication to provide treatment for a number of medical conditions including epileptic seizures (e.g., by use of Furosemide), high blood pressure (e.g., by use of calcium channel blockers, CCBs), elevated cholesterol (e.g., by use of LIPITOR), diabetes (e.g., by use of insulin), coronary arrhythmia's (both atrial and ventricular, e.g., by use of CCBss), coronary ischemia (e.g., by use of nitroglycerin or other vasodilating agent), or cerebral ischemia, heart attack or stroke (e.g., by use of aspirin, TPA or other hemolytic agent), anemia (e.g., by use of ferric-pyrophosphate) or other like conditions. Further embodiments of the invention can be used to provide concurrent treatment for two or more of these or other conditions eliminating the need for the patient to take multiple doses of different drugs (e.g., orally or by parenteral means) over the course of a day. This is particularly beneficial to patients who have long term chronic conditions including those who have impaired cognitive or physical abilities.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be sized and otherwise adapted for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for delivering a solid form medication comprising a drug, the method comprising:
storing a solid form medication within a container in the body of a patient for an extended period without substantial degradation or deleterious effect to the medication, wherein the medication comprises a drug for the treatment of a disease or condition; and
delivering the solid form medication from the container to a delivery site within the body so as to produce a therapeutic effect at a target tissue site for the treatment of the disease or condition wherein the delivering comprises transferring the solid form medication from the container to an outer chamber and through an opening in the outer chamber.

2. The method of claim 1, wherein the deleterious effect comprises a loss of potency or therapeutic effectiveness of the drug.

3. The method of claim 1, wherein the medication is in pellet form.

4. The method of claim 1, further comprising:
dissolving the delivered solid form medication at the delivery site to yield a therapeutically effective amount of the drug at the target tissue site.

5. The method of claim 4, wherein the rate of disintegration of the solid form medication at the delivery site is enhanced through the use of a disintegration enhancing feature in or on the solid form medication.

6. The method of claim 4, further comprising: determining a degradation state of the delivered solid form medication; and
delivering another dose of solid form medication responsive to the determined degradation state.

7. The method of claim 6, wherein the degradation state is determined using one of an optical, acoustical, or impedance sensor.

8. The method of claim 6, wherein the degradation state is determined by sending and receiving a signal from the delivered solid form medication.

9. The method of claim 8, wherein the signal is one of an optical, acoustic or electrical signal.

10. The method of claim 6, wherein the degradation state is combined with another parameter in determining whether to deliver another dose of medication.

11. The method of claim 10, wherein the other parameter is an in vivo concentration of the drug.

12. The method of claim 11, wherein the in vivo concentration is that at the delivery site, a target site, in blood or in cerebrospinal fluid.

13. The method of claim 10, wherein the other parameter is a dose frequency, a physiological parameter or a physiological parameter indicative of a medical condition or the onset of a medical condition.

14. The method of claim 1, wherein the medication comprises a pharmaceutical excipient.

15. The method of claim 14, wherein the excipient comprises a disintegrant configured to control a rate of disintegration of the solid medication at the delivery site.

16. The method of claim 14, wherein the excipient comprises a super disintegrant configured to accelerate a rate of disintegration of the solid medication at the delivery site.

17. The method of claim 1, further comprising:
delivering energy to the solid form medication to enhance a rate of disintegration of the solid form medication at the delivery site.

18. The method of claim 17, wherein the energy comprises thermal, electromagnetic, radiofrequency, acoustic or optical energy.

19. The method of claim 17, wherein the delivered energy produces structural defects in the solid form medication which enhance ingress of body tissue fluids into the solid form medication.

20. The method of claim 17, wherein the energy is delivered after the solid form medication is delivered to the delivery site.

21. The method of claim 1, wherein the target tissue site is at a different location from the delivery site.

22. The method of claim 21, wherein the target tissue site is non-appositional to the delivery site.

23. The method of claim 1, wherein the delivery tissue site is the brain, spinal cord, skeletal muscle, heart, lungs, liver, uterus, ovaries, testes, arteries, veins, prostate, blood, skin, thyroid gland, bone marrow, or kidney.

24. The method of claim 1, wherein the extended period is up to about one year.

25. The method of claim 1, wherein the extended period is up to about five years.

26. The method of claim 1, wherein the opening comprises the lumen of an elongate member, and delivering the solid form medication to the delivery site comprises delivering the solid form medication through the elongate member lumen to the delivery site.

27. The method of claim 1, wherein the elongate member has sufficient length to deliver the solid form medication to a different tissue location than the location of the container.

28. The method of claim 1, wherein the solid form medication is delivered from the container to the outer chamber using a drive source.

29. The method of claim 28, wherein the drive source comprises a linear inductance motor, a piezo-electric material, a solenoid, a shape memory wire, a fluidic drive source or a thermal drive source.

30. The method of claim 1, wherein the solid form medication is delivered at regular intervals.

31. The method of claim 30, wherein the interval is a daily, weekly or monthly interval.

32. The method of claim 1, wherein the solid form medication is delivered in response to a sensed biological parameter.

33. The method of claim 32, wherein the sensed biological parameter is predictive of a medical condition, a neurological seizure or an epileptic seizure.

34. The method of claim 1, wherein an interior of the container remains substantially isolated from the environment of the body during the extended period.

35. The method of claim 1, further comprising implanting the container at the delivery site in the body.

36. The method of claim 35, wherein at least a portion of the container is conformable, the method further comprising:
conforming the container to a shape of the delivery site.

37. The method of claim 35, wherein the container is implanted using minimally invasive methods.

38. The method of claim 1, wherein the drug comprises Furosemide.

39. The method of claim 1, wherein the drug comprises insulin.

40. The method of claim 1, wherein the drug comprises a vasodilating agent.

41. A method for delivering a solid form medication comprising a drug for the treatment of an epileptic seizure, the method comprising:
storing a solid form medication within a container implanted in the skull of a patient for an extended period without substantial degradation or deleterious effect to the medication, wherein the medication comprises a drug for the treatment of an epileptic seizure; and
delivering the solid form medication from the container to a delivery site within brain tissue so as to prevent an epileptic seizure or decrease the severity or duration of an epileptic seizure.

42. The method of claim 41, wherein the medication is in pellet form.

43. The method of claim 41, wherein the drug comprises Furosemide.

44. The method of claim 41, further comprising:
dissolving the delivered solid form medication within the cerebrospinal fluid (CSF) of the brain to achieve a selected concentration of the drug within the CSF to prevent the epileptic seizure or lessen the severity or duration of the epileptic seizure.

45. The method of claim 41, wherein the solid form medication is delivered in response to a sensed biological parameter predictive of an epileptic seizure.

* * * * *